United States Patent [19]
Tsutsumi et al.

[11] Patent Number: 6,087,149
[45] Date of Patent: Jul. 11, 2000

[54] STARCH CONVERSION PROCESS

[75] Inventors: Noriko Tsutsumi, Chiba-ken, Japan; Henrik Bisgård-Frantzen, Bagsværd; Allan Svendsen, Birkerød, both of Denmark

[73] Assignee: Novo Nordisk A/S, Bagsvaerd, Denmark

[21] Appl. No.: 09/129,075

[22] Filed: Aug. 4, 1998

Related U.S. Application Data

[63] Continuation of application No. PCT/DK98/00304, Jul. 2, 1998.
[60] Provisional application No. 60/055,867, Aug. 13, 1997.

[30] Foreign Application Priority Data

Feb. 7, 1997 [DK] Denmark .................................. 0787/97

[51] Int. Cl.$^7$ .............................. C12N 15/56; C12N 9/44; C12N 1/15; C12N 1/21; C12N 15/63
[52] U.S. Cl. .................... 435/210; 435/320.1; 435/252.3; 435/252.31; 435/252.33; 435/254.11; 435/254.2; 435/254.21; 435/254.22; 435/254.23; 435/254.3; 435/254.6; 435/254.7; 435/325; 536/23.1; 536/23.2
[58] Field of Search .................... 536/23.2, 23.1; 435/320.1, 252.3, 252.31, 252.33, 254.11, 254.2, 254.21, 259.22, 254.23, 254.3, 254.6, 254.7, 325, 210

[56] References Cited

U.S. PATENT DOCUMENTS

| | | | |
|---|---|---|---|
| 3,730,840 | 5/1973 | Sugimoto et al. | 195/31 R |
| 3,879,212 | 4/1975 | Yoshida et al. | 106/213 |
| 3,881,991 | 5/1975 | Kurimoto et al. | 195/31 R |

FOREIGN PATENT DOCUMENTS

| | | |
|---|---|---|
| 0 486 936 A1 | 5/1992 | European Pat. Off. . |
| 0 529 893 A1 | 3/1993 | European Pat. Off. . |
| 0 558 036 A1 | 9/1993 | European Pat. Off. . |
| 0 727 485 A1 | 8/1996 | European Pat. Off. . |
| 96/03513 | 2/1996 | WIPO . |

OTHER PUBLICATIONS

Maruta et al. (1996) Biochimica et Biophysica Acta 1291:177–181.

*Primary Examiner*—Rebecca E. Prouty
*Attorney, Agent, or Firm*—Steve T. Zelson, Esq.; Elias J. Lambiris, Esq.

[57] ABSTRACT

The present invention relates to a starch conversion process of the type which includes a debranching step wherein an isoamylase being active at the process conditions prevailing is used for debranching the starch and to the use of thermostable isoamylases for starch conversion. The invention further relates to an isolated isoamylase obtained from a strain of the genus Rhodothermus and to cloned DNA sequences encoding isoamylases derived from a strain of Rhodothermus or Sulfolobus, to expression vectors comprising said DNA sequence, host cells comprising such expression vectors, and finally to methods for producing said isoamylases.

23 Claims, 7 Drawing Sheets pFSI82

| TEST | LIQUEFACTION, 8μG/G DS, PH 5,5, STD. | | SACCHARIFICATION | | YIELDS | | | |
|---|---|---|---|---|---|---|---|---|
| | ADD. ISO-AMYLASE | INACTI-VATION | ADD. PROMOZYME | ADD. ISO-AMYLASE | DP1 | DP2 | DP3 | DP4+ |
| 1. ref./std. | None | yes | yes | none | 95.5% | 1.4% | 0.35% | 2.2% |
| 2. | none | no | yes | none | 96.3% | 1.3% | 1.2% | 1.0% |
| 3. | yes, 50 μg/g DS | no | yes | none | 96.5% | 1.3% | 1.0% | 0.8% |
| 4. | yes, 200 μg/g DS | no | yes | none | 96.8% | 1.4% | 0.9% | 0.6% |
| 5. ref. | none | yes | no | no | 93.2% | 1.7% | 0.5% | 4.7% |
| 6. | none | no | no | no | 94.0% | 1.6% | 1.8% | 2.2% |
| 7. | none | yes | no | yes, 50 μg/g DS | 94.8% | 1.8% | 0.4% | 3.0% |
| 8. | yes, 50 μg/g DS | no | no | no | 94.2% | 1.6% | 1.7% | 2.1% |
| 9. | yes, 200 μg/g DS | no | no | no | 94.2% | 1.7% | 1.7% | 2.0% |

Fig. 7

SEQUENCE LISTING

<160> NUMBER OF SEQ ID NOS: 16

<210> SEQ ID NO 1
<211> LENGTH: 22
<212> TYPE: DNA
<213> ORGANISM: Pseudomonas amyloderamosa
<220> FEATURE:
<221> NAME/KEY: misc_feature
<222> LOCATION: (0)...(0)
<223> OTHER INFORMATION: N is inosine

<400> SEQUENCE: 1
gnttyaaycc naayaarbtn yt                                           22

<210> SEQ ID NO 2
<211> LENGTH: 20
<212> TYPE: DNA
<213> ORGANISM: Pseudomonas amyloderamosa
<220> FEATURE:
<221> NAME/KEY: misc_feature
<222> LOCATION: (12)...(12)
<223> OTHER INFORMATION: N is inosine

<400> SEQUENCE: 2
ttratraccc cnatrtactg                                              20

<210> SEQ ID NO 3
<211> LENGTH: 2181
<212> TYPE: DNA
<213> ORGANISM: Rhodothermus marinus

<400> SEQUENCE: 3
atgtcacata gcgcgcaacc ggttacgtcg gtacaggccg tctggcccgg ccggccttat     60
ccgctgggtg ccacctggga cgggctgggc gtcaactttg ccctctacag ccagcacgcc    120
gaggcggtcg aactggtgct gttcgaccac ccggacgatc ccgcgccttc gcgcacgatc    180
gaagtgaccg aacggacagg cccgatctgg catgtgtacc tgcccggcct gcgtcccggc    240
cagctctacg gctatcgcgt ctacggaccc taccggccgg aggaaggcca ccgcttcaat    300

```
ccgaacaagg tgctgctcga ccccctacgcg aaggccatcg gccggcccct tcgctggcac    360
gacagcctct tcggttacaa aatcggcgat ccggccgggg atctgtcgtt ctccgaagaa    420
gacagcgctc cgtacgcgcc gctgggagcc gtcgtggagg gctgtttcga gtggggcgac    480
gaccgcccgc cgcgcattcc ctgggaagac acgatcatct acgaaacgca cgtcaagggc    540
atcacgaagc tgcatccgga agtgccggag ccgctgcggg ggacgtatct ggggctgacc    600
tgcgagccgg tgctggagca cctgaagcag ctgggcgtca ccacgatcca gctccttccg    660
gtgcacgcaa aagtgcacga tcggcacctg gtcgagcgcg gcctgcgcaa ctactggggc    720
tacaatccgc tctgctactt tgcgccggag cccgagtacg ccacgaacgg gccgatctcg    780
gccgtgcgcg agttcaagat gatggtgcgg gcgctgcatg ctgccggctt cgaggtgatc    840
gtcgacgtgg tctacaacca cacgggcgaa ggcggcgtgc tgggcccac gctgtcgttc    900 cggggcatcg acaaccgcgc ctactacaag gccgatccga caaacccgcg ctttctggtc    960
gattacacgg gcaccggcaa cacgctggac gtgggcaacc cctacgtcat ccagctcatc   1020
atggacagcc tgcgctactg ggtcactgaa atgcacgtcg acggctttcg gttcgacctg   1080
gccgccgcgc tggcccgcga gctgtacgac gtggacatgc tctcgacctt ttttcaggtc   1140
attcagcagg acccggtgct cagccaggtc aagctcatcg ccgaaccctg ggacgtcggg   1200
ccgggggggt atcaggtggg acattttccc tggcagtgga ccgagtggaa cggccgctat   1260
cgtgacgccg tgccgcgctt ctggcggggc gatcggggcc tcaacggtga gtttgccacg   1320
cgctttgccg gctccagcga tctgtacgaa cgtagcggtc gtcgtccgtt cgcttcgatc   1380
aacttcgtca cggcgcacga cggcttcacg ctggaagacc tggtcagcta cacgaaaaag   1440
cacaacgaag cgaatctgga aggcaaccgg gacggcatgg acgaaaacta cagcacgaac   1500
tgcggggtgg agggacccac gcaggatccg tccgtgctgg cctgccggga agcgctcaag   1560
cgcagcctga tcagcacgct ctttctctcg cagggcgtgc ccatgctgct gggcggcgac   1620
gagctgtcgc gcacgcagca cggcaacaac aacgcctatt gccaggacaa cgagatcagc   1680
tggtacaact ggcagctcga cacgcgcaag cagcagtttc tggagttcgt gcgccagacg   1740
atctggtttc gcaagcagca tcggagcttc cggcgccgcc attttctgac cggattgccc   1800
aacggcggaa ggccccgacg cagtctggtg gcacctgagg gtcggcccat gccacgag   1860 gactggacca acccggagct gacggccttc ggactgctgc tgcacggcga cgccattcag   1920
gggaccgacg agcacggacg accgtttcgc gacgacacgt ttctgattct gttcaacaac   1980
ggcagcgaag ccgtgccggt cgtggtgccg gaggtatgct cctgtggcaa gccgcaccac   2040
tgggaggtgg tcccggtgtt tcaacgcaat gtggagcccc ccacgtgcgc gcccggcgag   2100
acgctgtcgc tcccgcccgg cgtgctgacg gtgctggtgg ccgtaccgcc gttctcggat   2160
ggaaacacgg agccggcctg a                                              2181
```

<210> SEQ ID NO 4
<211> LENGTH: 726
<212> TYPE: PRT
<213> ORGANISM: Rhodothermus marinus

<400> SEQUENCE: 4

Met Ser His Ser Ala Gln Pro Val Thr Ser Val Gln Ala Val Trp Pro
 1               5                  10                  15

Gly Arg Pro Tyr Pro Leu Gly Ala Thr Trp Asp Gly Leu Gly Val Asn
            20                  25                  30

-continued

```
Phe Ala Leu Tyr Ser Gln His Ala Glu Ala Val Glu Leu Val Leu Phe
         35                  40                  45
Asp His Pro Asp Asp Pro Ala Pro Ser Arg Thr Ile Glu Val Thr Glu
 50                  55                  60
Arg Thr Gly Pro Ile Trp His Val Tyr Leu Pro Gly Leu Arg Pro Gly
 65                  70                  75                  80
Gln Leu Tyr Gly Tyr Arg Val Tyr Gly Pro Tyr Arg Pro Glu Glu Gly
                 85                  90                  95
His Arg Phe Asn Pro Asn Lys Val Leu Leu Asp Pro Tyr Ala Lys Ala
                100                 105                 110
Ile Gly Arg Pro Leu Arg Trp His Asp Ser Leu Phe Gly Tyr Lys Ile
            115                 120                 125
Gly Asp Pro Ala Gly Asp Leu Ser Phe Ser Glu Glu Asp Ser Ala Pro
130                 135                 140
Tyr Ala Pro Leu Gly Ala Val Val Glu Gly Cys Phe Glu Trp Gly Asp
145                 150                 155                 160
Asp Arg Pro Pro Arg Ile Pro Trp Glu Asp Thr Ile Ile Tyr Glu Thr
                165                 170                 175
His Val Lys Gly Ile Thr Lys Leu His Pro Glu Val Pro Glu Pro Leu
            180                 185                 190
Arg Gly Thr Tyr Leu Gly Leu Thr Cys Glu Pro Val Leu Glu His Leu
        195                 200                 205
Lys Gln Leu Gly Val Thr Thr Ile Gln Leu Leu Pro Val His Ala Lys
210                 215                 220
Val His Asp Arg His Leu Val Glu Arg Gly Leu Arg Asn Tyr Trp Gly
225                 230                 235                 240
Tyr Asn Pro Leu Cys Tyr Phe Ala Pro Glu Pro Glu Tyr Ala Thr Asn
                245                 250                 255
Gly Pro Ile Ser Ala Val Arg Glu Phe Lys Met Met Val Arg Ala Leu
            260                 265                 270
His Ala Ala Gly Phe Glu Val Ile Val Asp Val Val Tyr Asn His Thr
        275                 280                 285
Gly Glu Gly Gly Val Leu Gly Pro Thr Leu Ser Phe Arg Gly Ile Asp
290                 295                 300
Asn Arg Ala Tyr Tyr Lys Ala Asp Pro Asn Asn Pro Arg Phe Leu Val
305                 310                 315                 320
Asp Tyr Thr Gly Thr Gly Asn Thr Leu Asp Val Gly Asn Pro Tyr Val
                325                 330                 335
Ile Gln Leu Ile Met Asp Ser Leu Arg Tyr Trp Val Thr Glu Met His
            340                 345                 350
Val Asp Gly Phe Arg Phe Asp Leu Ala Ala Ala Leu Ala Arg Glu Leu
        355                 360                 365
Tyr Asp Val Asp Met Leu Ser Thr Phe Phe Gln Val Ile Gln Gln Asp
370                 375                 380
Pro Val Leu Ser Gln Val Lys Leu Ile Ala Glu Pro Trp Asp Val Gly
385                 390                 395                 400
Pro Gly Gly Tyr Gln Val Gly His Phe Pro Trp Gln Trp Thr Glu Trp
                405                 410                 415
Asn Gly Arg Tyr Arg Asp Ala Val Arg Arg Phe Trp Arg Gly Asp Arg
            420                 425                 430
Gly Leu Asn Gly Glu Phe Ala Thr Arg Phe Ala Gly Ser Ser Asp Leu
        435                 440                 445
Tyr Glu Arg Ser Gly Arg Arg Pro Phe Ala Ser Ile Asn Phe Val Thr
```

```
                    450                 455                 460
Ala His Asp Gly Phe Thr Leu Glu Asp Leu Val Ser Tyr Thr Lys Lys
465                 470                 475                 480

His Asn Glu Ala Asn Leu Glu Gly Asn Arg Asp Gly Met Asp Glu Asn
                485                 490                 495

Tyr Ser Thr Asn Cys Gly Val Glu Gly Pro Thr Gln Asp Pro Ser Val
                500                 505                 510

Leu Ala Cys Arg Glu Ala Leu Lys Arg Ser Leu Ile Ser Thr Leu Phe
                515                 520                 525

Leu Ser Gln Gly Val Pro Met Leu Leu Gly Gly Asp Glu Leu Ser Arg
                530                 535                 540

Thr Gln His Gly Asn Asn Asn Ala Tyr Cys Gln Asp Asn Glu Ile Ser
545                 550                 555                 560

Trp Tyr Asn Trp Gln Leu Asp Thr Arg Lys Gln Gln Phe Leu Glu Phe
                565                 570                 575

Val Arg Gln Thr Ile Trp Phe Arg Lys Gln His Arg Ser Phe Arg Arg
                580                 585                 590

Arg His Phe Leu Thr Gly Leu Pro Asn Gly Gly Arg Pro Arg Arg Ser
                595                 600                 605

Leu Val Ala Pro Glu Gly Arg Pro Met Arg His Glu Asp Trp Thr Asn
610                 615                 620

Pro Glu Leu Thr Ala Phe Gly Leu Leu Leu His Gly Asp Ala Ile Gln
625                 630                 635                 640

Gly Thr Asp Glu His Gly Arg Pro Phe Arg Asp Asp Thr Phe Leu Ile
                645                 650                 655

Leu Phe Asn Asn Gly Ser Glu Ala Val Pro Val Val Pro Glu Val
                660                 665                 670

Cys Ser Cys Gly Lys Pro His His Trp Glu Val Val Pro Val Phe Gln
                675                 680                 685

Arg Asn Val Glu Pro Pro Thr Cys Ala Pro Gly Glu Thr Leu Ser Leu
                690                 695                 700

Pro Pro Gly Val Leu Thr Val Leu Val Ala Val Pro Pro Phe Ser Asp
705                 710                 715                 720

Gly Asn Thr Glu Pro Ala
                725

<210> SEQ ID NO 5
<211> LENGTH: 26
<212> TYPE: DNA
<213> ORGANISM: Rodethermus marinus

<400> SEQUENCE: 5
gtcagtagcc catggcacat tagcgc                                      26

<210> SEQ ID NO 6
<211> LENGTH: 24
<212> TYPE: DNA
<213> ORGANISM: Rodethermus marinus

<400> SEQUENCE: 6
ctcggccgga ctagatctgt cttc                                        24

<210> SEQ ID NO 7
<211> LENGTH: 39
<212> TYPE: DNA
<213> ORGANISM: Sulfolobus acidocaldarius
```

-continued

```
<400> SEQUENCE: 7
gtatatcaaa gcttatgaaa gatcgaccat taaagcctg                                39

<210> SEQ ID NO 8
<211> LENGTH: 35
<212> TYPE: DNA
<213> ORGANISM: Sulfolobus acidocaldarius

<400> SEQUENCE: 8
ggttgtctag atcactggaa ctctatcctc ctgta                                    35

<210> SEQ ID NO 9
<211> LENGTH: 26
<212> TYPE: DNA
<213> ORGANISM: Artificial Sequence
<220> FEATURE:
<221> NAME/KEY: mutation
<222> LOCATION: (0)...(0)
<223> OTHER INFORMATION: Oligo 1

<400> SEQUENCE: 9
gatcaagctt ggaattcgct cgagct                                              26

<210> SEQ ID NO 10
<211> LENGTH: 26
<212> TYPE: DNA
<213> ORGANISM: Artificial Sequence
<220> FEATURE:
<221> NAME/KEY: mutation
<222> LOCATION: (0)...(0)
<223> OTHER INFORMATION: Oligo 2

<400> SEQUENCE: 10
ctagagctcg agcgaattcc aagctt                                              26

<210> SEQ ID NO 11
<211> LENGTH: 140
<212> TYPE: PRT
<213> ORGANISM: Flavobacterium sp.

<400> SEQUENCE: 11

Phe Asn Pro Asn Lys Leu Leu Asp Pro Tyr Ala Lys Ala Val His
 1               5                  10                  15

Arg Gln Ile Asp Trp Asp Pro Ala Leu Phe Ser Tyr Asn Leu Gly Asp
                20                  25                  30

Pro Asp Ser Arg Asn Asp Asp Ser Ala Pro His Met Met Leu Gly
            35                  40                  45

Val Val Ile Asn Pro Phe Phe Asp Trp Asp Gly Asp Lys Leu Pro Arg
    50                  55                  60

Ile Pro Tyr His Lys Ser Val Ile Tyr Glu Ala His Val Lys Gly Leu
65                  70                  75                  80

Thr Gln Leu His Pro Glu Val Pro Glu Gly Ala Ala Arg Tyr Tyr Ala
                85                  90                  95

Gly Val Ala His Pro Ala Val Ile Ser His Leu Gln Lys Leu Gly Ile
            100                 105                 110

Thr Ala Ile Glu Leu Met Pro Val His Gln Phe Val Asn Asp Gly Ile
        115                 120                 125

Leu Gln Asp Lys Gly Leu Asn Asn Tyr Trp Gly Tyr
            130                 135                 140

<210> SEQ ID NO 12
```

-continued

```
<211> LENGTH: 143
<212> TYPE: PRT
<213> ORGANISM: Flavobacterium devorans

<400> SEQUENCE: 12
```

Phe Asn Pro Asn Lys Val Leu Leu Asp Pro Tyr Ala Arg Lys Leu Phe
 1               5                  10                  15

Gly Glu Ile Lys Trp Thr Asp Ala Leu His Gly Tyr Gln Ile Arg Ser
            20                  25                  30

Lys Lys Glu Asp Leu Ser Phe Asp Lys Arg Asp Ser Ala Ala Ala Met
        35                  40                  45

Pro Lys Ala Val Val Asp Asp His Phe Asp Trp Ser Arg Asp Val
    50                  55                  60

Lys Pro Asn Thr Pro Trp Ser Glu Thr Val Ile Tyr Glu Ala His Val
65                  70                  75                  80

Lys Gly Leu Thr Lys Leu Met Glu Leu Val Pro Pro Arg Glu Arg Gly
                85                  90                  95

Thr Tyr Ala Gly Leu Gly His Pro Ala Val Ile Lys His Leu Lys Arg
            100                 105                 110

Ile Gly Val Thr Ala Ile Glu Leu Leu Pro Ile His Ser Phe Thr Gln
        115                 120                 125

Asp Arg Phe Leu Gln Glu Lys Gly Leu Arg Asn Tyr Trp Gly Tyr
    130                 135                 140

```
<210> SEQ ID NO 13
<211> LENGTH: 143
<212> TYPE: PRT
<213> ORGANISM: Xanthomonas camperstris

<400> SEQUENCE: 13
```

Phe Asn Pro Asn Lys Val Leu Leu Asp Pro Tyr Ala Arg Glu Leu Asp
 1               5                  10                  15

Gly Asp Leu Val Trp Ala Asp Glu Leu Tyr Gly Tyr Thr Val Gly His
            20                  25                  30

Pro Asp Gly Asp Leu Ser Phe Asp Glu Arg Asp Ser Ala Pro Phe Met
        35                  40                  45

Pro Lys Cys Val Val Glu Asp Thr Tyr Asp Trp Glu Asp Asp Ala
    50                  55                  60

Arg Leu Leu Lys Pro Trp Asn Glu Thr Val Ile Tyr Glu Thr His Val
65                  70                  75                  80

Arg Gly Tyr Thr Met Arg Asn Ala Gln Val Pro Glu Ala Val Arg Gly
                85                  90                  95

Thr Phe Ala Gly Leu Ala Gln Pro Ser Val Leu Gln Tyr Ile Lys Asp
            100                 105                 110

Leu Gly Ile Thr Ala Val Glu Leu Leu Pro Val His Ala Tyr Leu Asp
        115                 120                 125

Asp Gln His Leu Leu Asp Lys Gly Leu Arg Asn Tyr Trp Gly Tyr
    130                 135                 140

```
<210> SEQ ID NO 14
<211> LENGTH: 143
<212> TYPE: PRT
<213> ORGANISM: Rhodothermus obamensis

<400> SEQUENCE: 14
```

Phe Asn Pro Asn Lys Val Leu Leu Asp Pro Tyr Ala Lys Ala Ile Gly
 1               5                  10                  15

```
Arg Pro Leu Arg Trp His Asp Ser Leu Phe Gly Tyr Lys Ile Gly Asp
            20                  25                  30

Pro Ala Gly Asp Leu Ser Phe Ser Glu Glu Asp Ser Ala Pro Tyr Ala
            35                  40                  45

Pro Leu Gly Ala Val Val Glu Gly Cys Phe Glu Trp Gly Asp Asp Arg
        50                  55                  60

Pro Pro Arg Ile Pro Trp Glu Asp Thr Ile Ile Tyr Glu Thr His Val
65                      70                  75                  80

Lys Gly Ile Thr Lys Leu His Pro Glu Val Pro Glu Pro Leu Arg Gly
                85                  90                  95

Thr Tyr Leu Gly Leu Thr Cys Glu Pro Val Leu Glu His Leu Lys Arg
            100                 105                 110

Leu Gly Val Thr Thr Ile Gln Leu Leu Pro Val His Ala Lys Val His
            115                 120                 125

Asp Arg His Leu Val Glu Arg Gly Leu Arg Asn Tyr Trp Gly Tyr
            130                 135             140

<210> SEQ ID NO 15
<211> LENGTH: 8
<212> TYPE: PRT
<213> ORGANISM: Pseudomonas amyloderamosa

<400> SEQUENCE: 15

Arg Phe Asn Pro Asn Lys Leu Leu
1               5

<210> SEQ ID NO 16
<211> LENGTH: 7
<212> TYPE: PRT
<213> ORGANISM: Pseudomonas amyloderamosa

<400> SEQUENCE: 16

Asn Tyr Trp Gly Tyr Met Thr
1               5
```

STARCH CONVERSION PROCESS

CROSS-REFERENCE TO RELATED APPLICATIONS

This application is a continuation of PCT/DK98/00304 filed Jul. 2, 1998 which claims priority under 35 U.S.C. 119 of Danish application 0787/97 filed Jul. 2, 1997 and U.S. provisional application Ser. No. 60/055,867 filed Aug. 13, 1997, the contents of which are fully incorporated herein by reference.

FIELD OF THE INVENTION

The invention relates to a starch conversion process of the type which includes a debranching step. The invention also relates to the use of a thermostable isoamylase for debranching starch. The invention further relates to an isolated isoamylase obtained from a strain of the genus Rhodothermus, to cloned DNA sequences encoding isoamylases derived from a strain of Rhodothermus or Sulfolobus, to expression vectors comprising said DNA sequence, host cells comprising such expression vectors, and finally to methods for producing said isoamylases.

BACKGROUND OF THE INVENTION

Starches such as corn, potato, wheat, manioc and rice starch are used as the starting material in commercial large scale production of sugars, such as high fructose syrup, high maltose syrup, maltodextrins amylose, trehalose, G2–G8 oligosaccharides (including functional oligosaccharides) and other carbohydrate products such as fat replacers.

Degradation of Starch

Starch usually consists of about 80% amylopectin and 20% amylose. Amylopectin is a branched polysaccharide in which linear chains α-1,4 D-glucose residues are joined by α-1,6 glucosidic linkages. Amylopectin is partially degraded by α-amylase which hydrolyze the 1,4-α-glucosidic linkages into branched and linear oligosaccharides. Prolonged degradation of amylopectin by α-amylase results in the formation of so-called α-limit dextrins which are not susceptible to further hydrolysis by the α-amylase. Branched oligosaccharides can be hydrolyzed into linear oligosaccharides by a debranching enzyme. The remaining branched oligosaccharides can slowly be depolymerized to D-glucose by glucoamylase. Glucoamylase hydrolyse linear oligosaccharides fast into D-glucose.

Amylose is a linear polysaccharide built up of D-glucopyranose units linked together by α-1,4 glucosidic linkages. Amylose is degraded into linear oligosaccharides by α-amylase which are fast depolymerized into D-glucose by glucoamylase.

Enzymes

α-amylase

α-amylase (E.C. 3.2.1.1) with the systematically name 1,4-α-D-glucan glucanohydrolase is capable of hydrolysing starch and other linear and branched 1,4-glucosidic oligo- and polysaccharides. α-amylase acts on the substrate in a random manner. The reducing groups are liberated in the α-configuration.

Debranching Enzymes

Debranching enzymes, which can attack amylopectin are divided into two classes: isoamylases (E.C. 3.2.1.68) and pullulanases (E.C. 3.2.1.41), respectively. Isoamylase hydrolyses α-1,6-D-glucosidic branch linkages in amylopectin and β-limit dextrins and can be distinguished from pullulanases by the inability of isoamylase to attack pullulan, and by the limited action on α-limit dextrins.

Glucoamylase

Glucoamylase or glucan 1,4-α-glucosidase (E.C. 3.2.1.3) hydrolyzes the terminal 1,4-linked α-D-glucose residues successively from the non-reducing ends of the chains with release of β-D-glucose. The enzyme can also slowly hydrolyze 1,6-α-D-glucosidic bonds in isomaltose, panose and related oligosaccharides.

Starch Conversion

A "traditional" starch conversion process degrading starch to lower molecular weight carbohydrate components such as sugars or fat replacers includes a debranching step.

Starch to Sugar Conversion

In the case of converting starch into a sugar the starch is depolymerized. A such depolymerization process consists of a pretreatment step and two or three consecutive process steps, viz. a liquefaction process, a saccharification process and dependent on the desired end product optionally an isomerization process.

Pre-treatment of Native Starch

Native starch consists of microscopic granules which are insoluble in water at room temperature. When an aqueous starch slurry is heated, the granules swell and eventually burst, dispersing the starch molecules into the solution. During this "gelatinization" process there is a dramatic increase in viscosity. As the solids level is 30–40% in a typically industrial process, the starch has to be thinned or "liquefied" so that it can be handled. This reduction in viscosity is today mostly obtained by enzymatic degradation.

Liquefaction

During the liquefaction step, the long chained starch is degraded into branched and linear shorter units (maltodextrins) by an α-amylase (e.g. Termamyl™). The liquefaction process is carried out at 105–110° C. for 5 to 10 minutes followed by 1–2 hours at 95° C. The pH lies between 5.5 and 6.2. In order to ensure an optimal enzyme stability under these conditions, 1 mM of calcium is added (40 ppm free calcium ions). After this treatment the liquefied starch will have a "dextrose equivalent" (DE) of 10–15.

Saccharification

After the liquefaction process the maltodextrins are converted into dextrose by addition of a glucoamylase (e.g. AMG™) and a debranching enzyme, such as an isoamylase (U.S. Pat. No. 4,335,208) or a pullulanase (e.g. Promozyme™) (U.S. Pat. No. 4,560,651). Before this step the pH is reduced to a value below 4.5, maintaining the high temperature (above 95° C.) to inactivate the liquefying α-amylase to reduce the formation of short oligosaccharide called "panose precursors" which cannot be hydrolyzed properly by the debranching enzyme.

The temperature is lowered to 60° C., and glucoamylase and debranching enzyme are added. The saccharification process proceeds for 24–72 hours.

Normally, when denaturing the α-amylase after the liquefaction step about 0.2–0.5% of the saccharification product is the branched trisaccharide $6^2$-α-glucosyl maltose (panose) which cannot be degraded by a pullulanase. If active amylase from the liquefaction step is present during saccharification (i.e. no denaturing), this level can be as high as 1–2%, which is highly undesirable as it lowers the saccharification yield significantly.

Isomerization

When the desired final sugar product is e.g. high fructose syrup the dextrose syrup may be converted into fructose. After the saccharification process the pH is increased to a value in the range of 6–8, preferably pH 7.5, and the calcium is removed by ion exchange. The dextrose syrup is then converted into high fructose syrup using, e.g., an immmobilized glucoseisomerase (such as Sweetzyme™).

Starch to Fat Replacer Conversion

A "fat replacer" is a fat-like carbohydrate which is used as a functional replacement of fat in foods. Fat-replacers typically consist of short chained amylose of linear polymers containing from about 15 to 65 anhydroglucose units linked by α-1,4-D-glucosidic bonds. Such fat replacers may be produced by enzymatic debranching of starch. Methods for degrading the α-1,6-D-glucosidic bonds of starch to form short chain low molecular weight amylose by the use of debranching enzymes are described in e.g. U.S. Pat. No. 3,730,840 (Sugimoto), U.S. Pat. No. 3,881,991 (Kurimoto) and U.S. Pat. No. 3,879,212 (Yoshida). A further method of producing short chained amylose to be used as a fat replacer is described in EP 0,486,936-A1 (National Strach and Chemical Investment Holding Corporation).

SUMMARY OF THE INVENTION

It is the object of the present invention to provide a starch conversion process of the type which includes a debranching step which results in a reduced formation of the undesired trisaccharide panose. The invention also relates to a novel thermostable isoamylase suitable for use in the starch conversion process of the invention.

According to the invention the term "starch conversion process" include all processes where starch is degraded into carbohydrate components with a lower molecular weight.

The present inventors have found that the achievement of the above-mentioned object of the invention requires an isoamylase debranching enzyme which is active at the process condition prevailing.

In the first aspect the invention relates to a starch conversion process of the type which includes a debranching step wherein an isoamylase being active at the process conditions prevailing is used for debranching the starch.

In the second aspect the invention relates to the use of a thermostable isoamylase in starch conversion processes.

BRIEF DESCRIPTION OF THE DRAWING

FIG. 7 shows the effect of adding the *R. marinus* isoamylase during starch conversion on the DP1, DP2, DP3 and DP4+ yields.

DETAILED DESCRIPTION OF THE INVENTION

Figure 1:
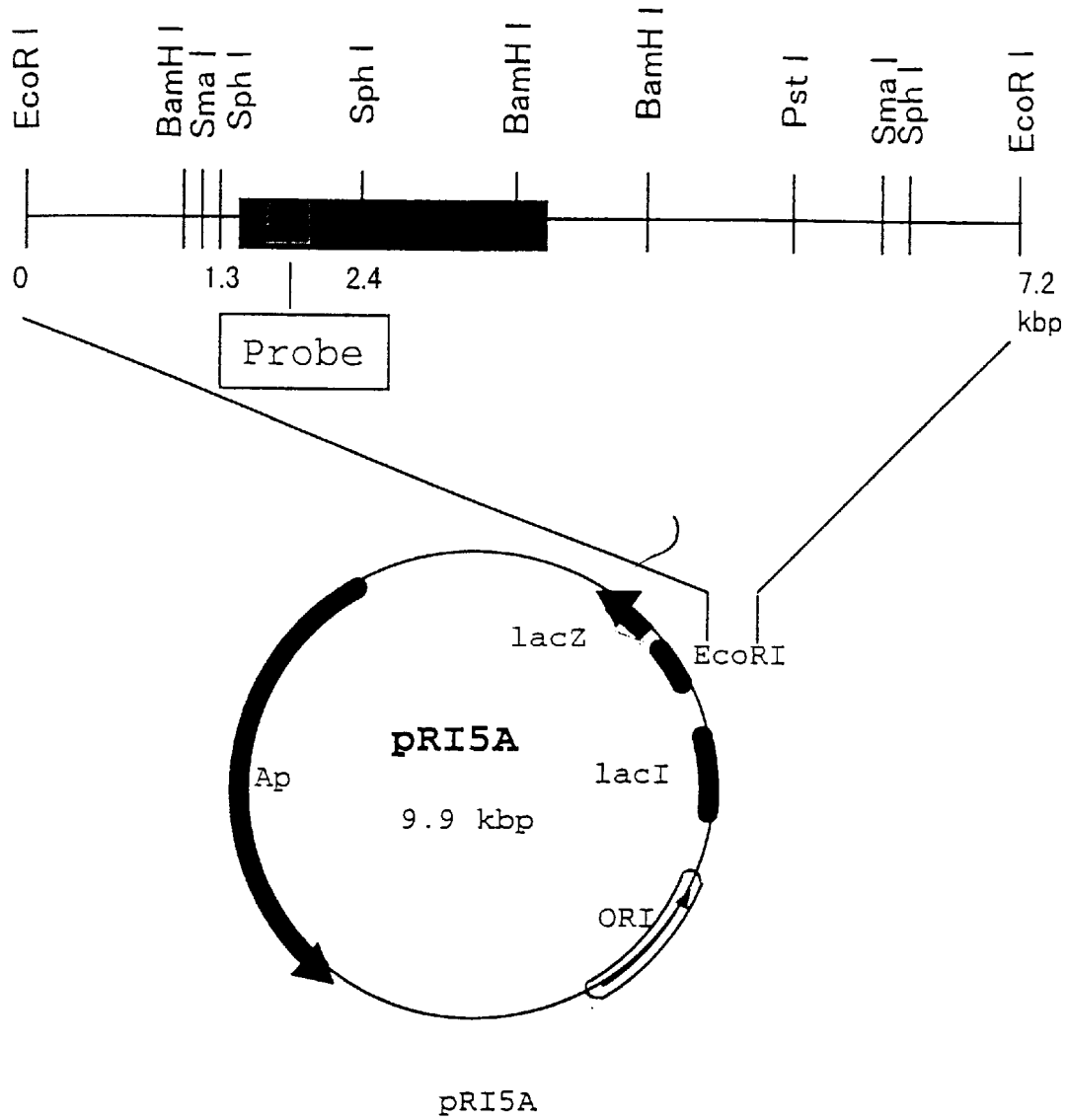
FIG. 1 shows the restriction enzyme map of pRI5A, the plasmid comprising the *Rhodothermus marinus* isoamylase.

It is the object of the present invention to provide a starch conversion process of the type which includes a debranching step which results in a reduced formation of the undesired trisaccharide panose. The invention also relates to a novel thermostable isoamylase suitable for use in the starch conversion process of the invention.

The present inventors have found that the achievement of the above-mentioned object of the invention requires an isoamylase debranching enzyme which is active at the process condition prevailing.

In the case of a starch depolymerization process the isoamylase should be active during liquefaction. This means that the isoamylase are substantially active at liquefaction temperatures, which lies from 95–110° C., especially around 105° C., at a pH in the range from 4.5 to 6.5, especially around pH 5.5.

In the context of the invention "substantially active" means that the relative enzymatic activity of the isoamylase is at least 50%, in particular at least 60%, especially at least 70%, such as at least 90%, or at least 95%, such as at least 99%, at 100° C. at pH 5.5 in comparison to the relative activity at the temperature optimum.

When the debranching takes place during liquefaction together with the action of an α-amylase the formation of panose precursors is reduced. By reducing the formation of panose precursors less panose will be present in the final product increasing the overall saccharification yield.

A thermostable isoamylase makes it possible to perform the liquefaction and the debranching at the same time before the saccharification step.

Specific examples of thermostable debranching enzymes are the thermostable isoamylases derived from the thermophilic bacteria such as *Sulfolobus acidocaldarius* ATCC 33909 (Maruta, K. et al., Biochimica et Biophysica Acta 1291, p. 177–181 (1996)), *Sulfolobus solfataricus* ATCC 35092 (accession number: Y08256) and *Rhodothermus marinus* DSM 4252 as will be described further below.

The Process

In the first aspect the invention relates to a starch conversion process of the type which includes a debranching step wherein an isoamylase being active at the process conditions prevailing is used for debranching the starch.

In an embodiment of the invention the starch conversion process is a starch depolymerization process wherein the isoamylase is active during the liquefaction step together with an α-amylase.

In a preferred embodiment the debranching enzyme being active at the process conditions prevailing is a thermostable isoamylase.

According to the invention the enzymatic degradation pattern in the traditional starch depolymerization process has been changed. Such an enzyme process change has not been possible before since all known isoamylases have been thermolabile and is inactivated at temperatures above 60° C.

According to the invention the liquefaction step is carried out at pH values adjusted to between 4.5 and 6.5, preferred 5.5 to 6.2, with e.g. sodium hydroxide, at temperatures of 95–110° C. for a period of 1 to 3 hours, preferably around 2 hours.

Optionally, if the α-amylase is calcium dependent calcium may be added in amounts of from 30 to 50 ppm, such as around 40 ppm (or 0.75 to 1.25 mM, such as around 1 mM), in the liquefaction step to stabilise the enzyme.

According to the invention the α-amylase need not be inactivated after the liquefaction step to reduced the panose formation.

Examples of specific α-amylases which can be used in the liquefaction step include *Bacillus licheniformis* α-amylases, such as the commercially available products Termamyl®, Spezyme® AA, Spezyme® Delta AA, Maxamyl®, Kleistase® and the α-amylase mutants described in WO 96/23874 (Novo Nordisk) and PCT/DK97/00197 (Novo Nordisk).

Isoamylases which can be used according to the invention include the thermostable isoamylase derived from the thermophilic archaebacteria *Sulfolobus acidocaldarius, Sulfolobus solfataricus* and the thermophilic eubacterium *Rhodothermus marinus* (as will be described in details below).

According to the invention the saccharification step is carried out at temperatures from 55 to 65° C. preferably around 60° C. by a glucoamylase for 24–72 hours. Examples of suitable glucoamylases include *Aspergillus niger* glucoamylases, such as AMG™ from e.g. Novo Nordisk.

In the case of the desired final sugar product is e.g. a high fructose syrup of approx. 50% fructose syrup the formed D-glucose is isomerized by an isomerase at a pH around 6–8, preferably pH 7.5.

Calcium is removed if added before the liquefaction step.

An examples of a suitable isomerases is an glucose isomerase such as the glucose isomerase derived from *Streptomyces murinus*. The isomerase may be an immmobilized glucose isomerase, such as Sweetzyme® (from Novo Nordisk)

Use

In the second aspect the invention relates to the use of a thermostable isoamylase in starch conversion processes, including fructose syrup conversion processes and for producing fat replacers.

In the case of the starch conversion process is a starch depolymerization process the thermostable isoamylase is used in combination with an α-amylase during the liquefaction step. The thermostable isoamylase may be derived from the thermophilic archaebacteria *Sulfolobus acidocaldarius* or *Sulfolobus solfataricus* or from *Rhodothermus marinus*.

The thermostable isoamylase may be used during the liquefaction step of a starch to glucose syrup or fructose syrup conversion process. The thermostable isoamylase may also be used in processes for producing fat replacers from starch.

Advantages of the Invention

In traditional starch conversion processes, such as starch depolymerization processes, the formation of the undesired side product, panose, has a significant influence on the overall saccharification yield. It is therefore desirable to reduce the formation of panose to increase the saccharification yield.

Several advantages are obtained by the addition of a thermostable isoamylase.

For instance, when the debranching of the starch takes place together with α-amylase in the liquefaction step of starch depolymerization, it is possible to extend the liquefaction process time without risking formation of large amount of panose precursors.

As the debranching enzyme is a thermostable isoamylase the debranching by a pullulanase during saccharification can be left out. This is advantageous as pullulanase tends to condense maltose into a panose precursor, $6^2$-α-maltosylmaltose which is hydrolysed into panose by glucoamylase.

By prolonging the liquefaction step the DE is increased from 10–15 to e.g. 15–20 reducing the need for glucoamylase (e.g. AMG™). This reduced glucoamylase requirement is advantageous as the formation of isomaltose is reduced. Isomaltose is formed from D-glucose resulting from depolymerization of linear oligosaccharides by glucoamylase which removes D-glucose from the non-reducing chain-ends. All together less glucoamylase activity results in an increased glucose yield.

Further, the saving of glucoamylase in the process of the invention enables the saccharification step to be carried out at a higher substrate concentration which is advantageous as the evaporation costs can be reduced.

Furthermore, when using the process of the invention for depolymerization the α-amylase used in the liquefaction process needs not be inactivated/denatured.

The saccharification reaction time can also be reduced significantly thereby increasing production capacity.

One aim of the present invention is to reduce the formation of panose.

In starch depolymerization processes this increases the saccharification yield as the addition of an isoamylase being active during the liquefaction step reduces the amount of formed panose precursors.

When using a thermostable isoamylase up front in the liquefaction process the process is less dependent of the specificity of the α-amylase and the formation of the panose precursors. This change allows an increased process time for the liquefaction and a higher DX than the normal value of DX 10–12 is obtained. If a more intensive liquefaction is allowed and a higher DX value is obtained by the use of a thermostable debranching enzyme its possible to increase the concentration of Dry Substance (DS) from the normal 30–35% to a higher percentage. Such an increase in %DS is advantageous as the evaporation costs are reduced significantly downstream in the High Fructose Corn Syrup (HFCS) process.

How to Identify Suitable Thermostable Isoamylases

Suitable thermostable isoamylases may be identified as described in Example 1 by first identifying conserved regions of amino acid sequence by aligning isoamylase sequences available. On the basis of the conserved regions PCR primers are designed. Genomic DNA stocks of a number of bacterial strains are then subjected to PCR, and strains yielding a fragment of the expected size are selected. The fragments are purified, sequenced, and aligned to confirm the homology with published isoamylase sequences. Among the strains identified, ones with the highest optimum growth temperature are further selected.

Using this approach isoamylases from *Rhodothermus marinus* DSM 4252 and *Rhodothermus obamensis* JCM 9785 were selected, and *R. marinus* isoamylase was further cloned as described in Example 2.

Novel Isoamylase Obtained from *Rhodothezrmus marinus* DSM 4252

As also indicated above the present inventors have found that an enzyme exhibiting isoamylase activity may be obtained from a strain of the genus Rhodothermus, more specifically *Rhodothermus marinus,* especially *Rhodothermus marinus* DSM 4252, and have succeeded in cloning a DNA sequence encoding said enzyme.

Comparison with Prior Art

A homology search with the isoamylase of the invention against nucleotide and protein databases was performed.

| Origins of isoamylase genes | identity | |
|---|---|---|
| | DNA | a.a. |
| Pseudomonas amyloderamosa*1 | 50.4% | 33.0% |
| Pseudomonas sp. SMP1*2 | 50.4% | 33.0% |
| Flavobacterium sp.*3 | 54.0% | 34.1% |
| Flavobacterium odoratum*4 | 54.8% | 36.6% |
| Sulfolobus acidocaldarius*5 | 51.8% | 54.2% |
| Sulfolobus solfataricus*6 | 51.1% | 55.0% |

*1: Table 1, 1
*2: Table 1, 2
*3: Table 1, 3
*4: Table 1, 4
*5: Table 1, 5
*6: GenBank: Accession number; Y08256

The homology search showed that the most related known sequence(s) were isoamylases from *Sulfolobus acidocaldarius* and *Sulfolobus solfataricus*. The DNA sequence of the invention (SEQ ID NO: 3) encoding an isoamylase shows about 51–52% DNA homology to the known isoamylase sequences from *Sulfolobus acidocaldarius* and *Sulfolobus solfataricus* and the corresponding amino acid sequence of the isoamylase of the invention (SEQ ID NO: 4) shows about 54–55% homology to a deduced amino acid sequence based on the known DNA sequence above.

This shows that a DNA and/or an amino acid sequence of a isoamylase of the invention indeed is distant from any known DNA and/or the amino acid sequence(s) encoding an isoamylase.

The calculation of homology was done as described later in this specification.

DEFINITIONS

Prior to discussing this invention in further detail, the following terms will first be defined.

"A cloned DNA sequence": The term "A cloned DNA sequence", refers to a DNA sequence cloned in accordance with standard cloning procedures used in genetic engineering to relocate a segment of DNA from its natural location to a different site where it will be reproduced. The cloning process involves excision and isolation of the desired DNA segment, insertion of the piece of DNA into the vector molecule and incorporation of the recombinant vector into a cell where multiple copies or clones of the DNA segment will be replicated.

The "cloned DNA sequence" of the invention may alternatively be termed "DNA construct" or "isolated DNA sequence".

"Obtained from": For the purpose of the present invention the term "obtained from" as used herein in connection with a specific microbial source, means that the enzyme is produced by the specific source, or by a cell in which a gene from the source have been inserted.

"An isolated polypeptide": As defined herein the term, "an isolated polypeptide" or "isolated isoamylase", as used about the isoamylase of the invention, is an isoamylase or isoamylase part which is at least about 20% pure, preferably at least about 40% pure, more preferably about 60% pure, even more preferably about 80% pure, most preferably about 90% pure, and even most preferably about 95% pure, as determined by SDS-PAGE. The term "isolated polypeptide" may alternatively be termed "purified polypeptide".

"Homologous impurities": As used herein the term "homologous impurities" means any impurity (e.g. another polypeptide than the enzyme of the invention) which originate from the homologous cell where the enzyme of the invention is originally obtained from. In the present invention the homologous cell may e.g. be a strain of Rhodothermus.

"Isoamylase encoding part": As used herein the term "isoamylase encoding part" used in connection with a DNA sequence means the region of the DNA sequence which corresponds to the region which is translated into a polypeptide sequence.

In the DNA sequence shown in SEQ ID NO: 3 it is the region between the first "ATG" start codon ("AUG" codon in mRNA) and the following stop codon ("TAA", "TAG" or "TGA"). In others words this is the translated polypeptide.

"isoamylase" in the present context is defined according to the Enzyme classification (EC), as having the EC-number: 3.2.1.68.

Characterisation of the Novel Thermostable Isoamylase from *Rhodothermus marinus*

Isolated Isoamylase

Accordingly, in a third aspect the invention relates to an isolated polypeptide having isoamylase activity which is obtained from a strain of the genus Rhodothermus and has i) isoamylase activity in the pH range of 3.5 to 6.5 and an optimum at around pH 5, measured at 50° C.;

ii) a molecular mass of about 80 kDa, as determined by SDS-PAGE; an isoelectric point (pI) in the range of 5.2–5.8.

An isoamylase of the invention obtained from a Rhodothermus sp. has been intensively characterised.

In a preferred embodiment the enzyme according to the first aspect of the invention is obtained from a strain of *Rhodothermus marinus*, especially *Rhodothermus marinus* DSM 4252.

In a preferred embodiment the enzyme according to the first aspect has the mature amino acid sequence shown as position 1–726 in SEQ ID NO: 4.

Isolated Enzyme

In a fourth aspect the invention relates to an isolated enzyme exhibiting isoamylase activity selected from the group consisting of:

(a) a polypeptide encoded by the isoamylase enzyme encoding part of the DNA sequence cloned into plasmid pUC19 present in *Escherichia coli* DSM 11971;

(b) a polypeptide comprising an amino acid sequence as shown in positions 1–726 of SEQ ID NO: 4;

(c) an analogue of the polypeptide defined in (a) or (b) which is at least 70% homologous with said polypeptide; and (d) a fragment of (a), (b) or (c).

The enzyme according this aspect of the invention may be obtained from a microorganism such as a bacterium, a yeast or a filamentous fungus. Preferably it is obtained from a bacteria.

Examples of suitable ones are given in the section "Microbial sources" (vide infra).

Cloned DNA Sequence from *Rhodothomus marinus*

In its fifth aspect the invention relates to a cloned DNA sequence encoding an enzyme exhibiting isoamylase activity, which DNA sequence comprises:

(a) the isoamylase encoding part of the DNA sequence cloned into plasmid pUC19 present in *Escherichia coli* DSM 11971;

(b) the DNA sequence shown in positions 1–2178 in SEQ ID NO: 3 or its complementary strand;

(c) an analogue of the DNA sequence defined in (a) or (b) which is at least 70% homologous with said DNA sequence;

(d) a DNA sequence which hybridises with a double-stranded DNA probe comprising the sequence shown in positions 1–2178 (encoding the mature part of the enzyme) in SEQ ID NO: 3 at low stringency;

(e) a DNA sequence which, because of the degeneracy of the genetic code, does not hybridise with the sequences of (b) or (d), but which codes for a polypeptide having the same amino acid sequence as the polypeptide encoded by any of these DNA sequences; or (f) a DNA sequence which is a fragment of the DNA sequences specified in (a), (b), (c), (d), or (e).

It is presently believed that the isoamylase encoding part of the DNA sequence cloned into plasmid pUC19 present in strain DSM 11971 is identical to the isoamylase encoding part of the DNA sequence presented in SEQ ID NO: 3.

Accordingly, the terms "the isoamylase encoding part of the DNA sequence cloned into plasmid pUC19 present in DSM 11971" and "the isoamylase encoding part of the DNA sequence presented in SEQ ID NO: 3" may be used interchangeably.

The DNA sequence may be of genomic, cDNA, or synthetic origin or any combination thereof.

The present invention also encompasses a cloned DNA sequence which encodes an enzyme exhibiting isoamylase activity having the amino acid sequence set forth as the mature part of SEQ ID NO: 4 (i.e. position 1–726), which DNA sequence differs from SEQ ID NO: 3 by virtue of the degeneracy of the genetic code.

The DNA sequence shown in SEQ ID NO: 3 and/or an analogue DNA sequence of the invention may be obtained from a microorganism such as a bacteria, a yeast or a filamentous fungus. Preferably it is obtained from a filamentous fungus and examples of suitable ones are given in the section "Microbial sources" (vide infra).

Alternatively, the analogous sequence may be constructed on the basis of the DNA sequence presented as the isoamylase encoding part of SEQ ID NO: 3, e.g. be a sub-sequence thereof and/or be constructed by introduction of nucleotide substitutions which do not give rise to another amino acid sequence of the isoamylase encoded by the DNA sequence, but which correspond to the codon usage of the host organism intended for production of the enzyme, or by introduction of nucleotide substitutions which may give rise to a different amino acid sequence (i.e. a variant of the isoamylase of the invention).

When carrying out nucleotide substitutions, amino acid changes are preferably of a minor nature, i.e. conservative amino acid substitutions that do not significantly affect the folding or activity of the protein, small deletions, typically of one to about 30 amino acids; small amino- or carboxyl-terminal extensions, such as an amino-terminal methionine residue; a small linker peptide of up to about 20–25 residues; or a small extension that facilitates purification, such as a poly-histidine tract; an antigenic epitope or a binding domain.

Examples of conservative substitutions are within the group of basic amino acids, such as arginine, lysine, histidine; acidic amino acids, such as glutamic acid and aspartic acid; polar amino acids, such as glutamine and asparagine; hydrophobic amino acids, such as leucine, isoleucine, valine; aromatic amino acids, such as phenylalanine, tryptophan, tyrosine; and small amino acids, such as glycine, alanine, serine, threonine, methionine. For a general description of nucleotide substitution, see e.g. Ford et al., (1991), Protein Expression and Purification 2, 95–107.

It will be apparent to persons skilled in the art that such substitutions can be made outside the regions critical to the function of the molecule and still result in an active polypeptide. Amino acids essential to the activity of the polypeptide encoded by the cloned DNA sequence of the invention, and therefore preferably not subject to substitution may be identified according to procedures known in the art, such as site-directed mutagenesis or alanine-scanning mutagenesis (cf. e.g. Cunningham and Wells, (1989), Science 244, 1081–1085). In the latter technique mutations are introduced at every residue in the molecule, and the resultant mutant molecules are tested for biological (i.e. isoamylase) activity to identify amino acid residues that are critical to the activity of the molecule. Sites of substrate-enzyme interaction can also be determined by analysis of crystal structure as determined by such techniques as nuclear magnetic resonance analysis, crystallography or photo affinity labelling (cf. e.g. de Vos et al., (1992), Science 255, 306–312; Smith et al., (1992), J. Mol. Biol. 224, 899–904; Wlodaver et al., (1992), FEBS Lett. 309, 59–64).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include, ligating the coding sequences encoding the polypeptides so that they are in frame and that expression of the fused polypeptide is under control of the same promoter(s) and terminator.

Homology of DNA Sequences

The DNA sequence homology referred to above is determined as the degree of identity between two sequences indicating a derivation of the first sequence from the second. The homology may suitably be determined by means of computer programs known in the art, such as GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443–453). Using GAP with the following settings for DNA sequence comparison: GAP creation penalty of 5.0 and GAP extension penalty of 0.3, the coding region of the analogous DNA sequences referred to above exhibits a degree of identity preferably of at least 70%, more preferably at least 80%, more preferably at least 90%, more preferably at least 95%, more preferably at least 97% with the isoamylase encoding part of the DNA sequence shown in SEQ ID NO: 3.

Hybridization

The hybridization conditions referred to above to define an analogous DNA sequence as defined in d) above which hybridizes to a double-stranded DNA probe comprising the sequence shown in positions 1–2178 in SEQ ID NO: 3 (i.e. the isoamylase encoding part of SEQ ID NO: 4), under at least low stringency conditions, but preferably at medium or high stringency conditions are as described in detail below.

Suitable experimental conditions for determining hybridization at low, medium, or high stringency between a nucleotide probe and a homologous DNA or RNA sequence involves presoaking of the filter containing the DNA fragments or RNA to hybridize in 5× SSC (Sodium chloride/Sodium citrate, Sambrook et al. 1989) for 10 min, and prehybridization of the filter in a solution of 5× SSC, 5× Denhardt's solution (Sambrook et al. 1989), 0.5% SDS and 100 μg/ml of denatured sonicated salmon sperm DNA (Sambrook et al. 1989), followed by hybridization in the same solution containing a concentration of 10 ng/ml of a random-primed (Feinberg, A. P. and Vogelstein, B. (1983) *Anal. Biochem.* 132:6–13), $^{32}$P-dCTP-labeled (specific activity>1×10$^9$ cpm/pg) probe for 12 hours at ca. 45° C. The filter is then washed twice for 30 minutes in 2× SSC, 0.5% SDS at least *55° C. (low stringency), more preferably at least 60° C. (medium stringency), still more preferably at least 65° C. (medium/high stringency), even more preferably at least 70° C. (high stringency), and even more preferably at least 75° C. (very high stringency).

Molecules to which the oligonucleotide probe hybridizes under these conditions are detected using a x-ray film.

It has been found that it is possible to theoretically predict whether or not two given DNA sequences will hybridize under certain specified conditions.

Accordingly, as an alternative to the above described experimental method the determination whether or not an analogous DNA sequence will hybridize to the nucleotide probe described above, can be based on a theoretical calculation of the Tm (melting temperature) at which two heterologous DNA sequences with known sequences will hybridize under specified conditions (e.g. with respect to cation concentration and temperature).

In order to determine the melting temperature for heterologous DNA sequences (Tm(hetero)) it is necessary first to determine the melting temperature (Tm(homo)) for homologous DNA sequences.

The melting temperature Tm(homo) between two fully complementary DNA strands (homoduplex formation) may be determined by use of the following formula, Tm(homo)=81.5° C.+16.6(log M)+0.41(%GC)−0.61 (% form)− 500/L ("Current protocols in Molecular Biology". John Wiley and Sons, 1995), wherein "M" denotes the molar cation concentration in wash buffer, "%GC" % Guanine (G) and Cytosine (C) of total number of bases in the DNA sequence, "% form" % formamid in the wash buffer, and "L" the length of the DNA sequence.

Using this formula and the experimental wash conditions given above, Tm(homo) for the homoduplex formation of the nucleotide probe corresponding to the DNA sequence shown in SEQ ID NO: 3, i.e. nucleotides 1–2178 is:

Tm(homo)=81.5+16.6 (log 0.30)+0.41(65)−0.61(0)−(500/2178)

Tm(homo)=99.2° C.

"M": 2× SSC corresponds to a cation conc. of 0.3M.

"%GC" The %GC in SEQ ID NO: 3 is 65.

"% form": There is no formamid in the wash buffer.

"L": The length of SEQ ID NO: 3 is 2178.

The Tm determined by the above formula is the Tm of a homoduplex formation (Tm(homo)) between two fully complementary DNA sequences. In order to adapt the Tm value to that of two heterologous DNA sequences, it is assumed that a 1% difference in nucleotide sequence between the two heterologous sequences equals a 1° C. decrease in Tm ("Current protocols in Molecular Biology". John Wiley and Sons, 1995). Therefore, the Tm(hetero) for the heteroduplex formation is found by subtracting the homology % difference between the analogous sequence in question and the nucleotide probe described above from the Tm(homo). The DNA homology percentage to be subtracted is calculated as described herein (vide supra).

With the experimental conditions above and a wash temperature of *55° C. (low stringency), an analogous sequence with 55.8% (100−(99.2−55)=55.8) homology will be considered to hybridize to the nucleotide probe described above. With the more preferably wash temperature at 65° C. (medium stringency) an analogous sequence with 65.8% homology will hybridize etc.

Homology to Amino Acid Sequences

The polypeptide homology referred to above (property (c)) of the polypeptide of the invention is determined as the degree of identity between two sequences indicating a derivation of the first sequence from the second. The homology may suitably be determined by means of computer programs known in the art such as GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443–453). Using GAP with the following settings for polypeptide sequence comparison: GAP creation penalty of 3.0 and GAP extension penalty of 0.1, the mature part of a polypeptide encoded by an analogous DNA sequence of the invention exhibits a degree of identity preferably of at least 70%, more preferably at least 80%, more preferably at least 90%, more preferably at least 95%, and especially at least 97% with the mature part of the amino acid sequence shown in SEQ ID NO: 4, i.e. position 1–726 in SEQ ID NO: 4.

The present invention is also directed to isoamylase variants which have an amino acid sequence which differs by no more than three amino acids, preferably by no more than two amino acids, and more preferably by no more than one amino acid from the mature part of the amino acid sequence set forth in SEQ ID NO: 4.

Immunological Cross-Reactivity

Antibodies to be used in determining immunological cross-reactivity may be prepared by using a purified enzymX. More specifically, antiserum against the enzymX of the invention may be raised by immunizing rabbits (or other rodents) according to the procedure described by N. Axelsen et al. in A Manual of Quantitative Immunoelectrophoresis, Blackwell Scientific Publications, 1973, Chapter 23, or A. Johnstone and R. Thorpe, Immunochemistry in Practice, Blackwell Scientific Publications, 1982 (more specifically p. 27–31). Purified immunoglobulins may be obtained from the antiserum obtained, for example by salt precipitation ((NH$_4$)$_2$ SO$_4$), followed by dialysis and ion exchange chromatography, e.g. on DEAE-Sephadex. Immunochemical characterization of proteins may be performed either by Outcherlony double-diffusion analysis (O. Ouchterlony in: Handbook of Experimental Immunology (D. M. Weir, Ed.), Blackwell Scientific Publications, 1967, pp. 655–706), by crossed immunoelectrophoresis (N. Axelsen et al., supra, Chapters 3 and 4), or by rocket immunoelectrophoresis (N. Axelsen et al., Chapter 2).

Microbial Sources

At the priority date of the present invention, the taxonomy applied below are in accordance with the World Wide web (WWW) NCBI taxonomy browser.

It is expected that a DNA sequence coding for a homologous enzyme, i.e. an analogous DNA sequence, is obtainable from other micro-organisms. For instance, the DNA sequence may be derived by similarly screening a cDNA/genomic DNA library of another micro-organism, in particular a bacteria, such as a strain of the order Cytophagales, such as a strain of Rhodothermus sp., in particular a strain of *R. marinus* or *R. obamensis,* especially *R. marinus* DSM 4252.

Deposited Strain

The complete full length DNA sequence encoding the isoamylase cloned from *Rhodothermus marinus* DSM 4252 has been transformed into a strain of the bacterium *E. coli* DH12S, comprised in the plasmid pUC19. Said transformant has been deposited by the inventors according to the Budapest Treaty on the International Recognition of the Deposit of Microorganisms for the Purposes of Patent Procedure at the Deutshe Sammlung von Mikroorganismen und Zellkulturen GmbH., Mascheroder Weg 1b, D-38124 Braunschweig Federal Republic of Germany, (DSM).

Deposit date: 29.01.98

Depositor's ref.: NN049374

DSM designation: *Escherichia coli* DSM 11971

Being an International Depository Authority under the Buda-pest Treaty, Deutshe Sammlung von Mikroorganismen und Zell-kulturen GmbH., affords permanence of the deposit in accordance with the rules and regulations of said treaty, vide in particular Rule 9. Access to the two deposits will be available during the pendency of this patent application to one determined by the Commisioner of the United States Patent and Trademark Office to be entitled thereto under 37 C.F.R. Par. 1.14 and 35 U.S.C. Par. 122. Also, the above mentioned deposits fulfill the requirements of European patent applications relating to micro-organisms according to Rule 28 EPC.

The above mentioned deposit represents a substantially pure culture of the isolated bacteria. The deposit is available as required by foreign patent laws in countries wherein counter-parts of the subject application, or its progeny are filed. However, it should be understood that the availability of the deposited strain does not constitute a license to practice the subject invention in derogation of patent rights granted by governmental action.

The DNA sequence of the invention, having the nucleotide sequence shown in SEQ ID NO: 3, can be cloned from the above mentioned strain *Escherichia coli* DSM 11971 using standard cloning techniques e.g. as described by Sambrook et al., (1989), Molecular Cloning: A Laboratory Manual. Cold Spring Harbor Lab.; Cold Spring Harbor, N.Y.

The DNA sequence of the invention can also be cloned by any general method involving cloning, in suitable vectors, a genomic DNA library from any organism expected to produce the isoamylase of interest, transforming suitable *E. coli* host cells with said vectors, culturing the host cells under suitable conditions to express any enzyme of interest encoded by a clone in the genomic DNA library, and isolating the enzyme encoding DNA from such clones.

A more detailed description of the screening method is given in a working example herein (vide infra).

Alternatively, the DNA encoding an isoamylase of the invention may, in accordance with well-known procedures, conveniently be cloned from a suitable source, such as any of organisms mentioned in the section "Microbial Sources", by use of hybridization to synthetic oligonucleotide probes prepared on the basis of a DNA sequence disclosed herein. For instance, a suitable oligonucleotide probe may be prepared on the basis of or preferably be the isoamylase encoding part of the nucleotide sequences presented as SEQ ID NO: 3 or any suitable sub-sequence thereof, or the basis of the amino acid sequence SEQ ID NO: 4.

Alternatively, the DNA sequence may be cloned by use of PCR primers prepared on the basis of the DNA sequence disclosed herein.

Recombinant Expression Vectors

A recombinant vector comprising a DNA construct encoding the enzyme of the invention may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome in part or in its entirety and replicated together with the chromosome(s) into which it has been integrated.

The vector is preferably an expression vector in which the DNA sequence encoding the enzyme of the invention is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the enzyme.

The promoter may be any DNA sequence which shows transcriptional activity in the host cell of choice and may be derived from genes encoding proteins either homologous or heterologous to the host cell.

Examples of suitable promoters for use in bacterial host cells include the promoter of the *Bacillus stearothermophilus* maltogenic amylase gene, the *Bacillus licheniformis* alpha-amylase gene, the *Bacillus amyloliquefaciens* alpha-amylase gene, the *Bacillus subtilis* alkaline protease gen, or the *Bacillus pumilus* xylosidase gene, or the phage Lambda $P_R$ or $P_L$ promoters or the *E. coli* lac, trp or tac promoters.

The DNA sequence encoding the enzyme of the invention may also, if necessary, be operably connected to a suitable terminator.

The recombinant vector of the invention may further comprise a DNA sequence enabling the vector to replicate in the host cell in question.

The vector may also comprise a selectable marker, e.g. a gene the product of which complements a defect in the host cell, or a gene encoding resistance to e.g. antibiotics like kanamycin, chloramphenicol, erythromycin, tetracycline, spectinomycine, or the like, or resistance to heavy metals or herbicides.

To direct an enzyme of the present invention into the secretory pathway of the host cells, a secretory signal sequence (also known as a leader sequence, prepro sequence or pre sequence) may be provided in the recombinant vector. The secretory signal sequence is joined to the DNA sequence encoding the enzyme in the correct reading frame. Secretory signal sequences are commonly positioned 5' to the DNA sequence encoding the enzyme. The secretory signal sequence may be that normally associated with the enzyme or may be from a gene encoding another secreted protein.

The procedures used to ligate the DNA sequences coding for the present enzyme, the promoter and optionally the terminator and/or secretory signal sequence, respectively, or to assemble these sequences by suitable PCR amplification schemes, and to insert them into suitable vectors containing the information necessary for replication or integration, are well known to persons skilled in the art (cf., for instance, Sambrook et al., op.cit.).

Host Cells

The DNA sequence encoding the present enzyme introduced into the host cell may be either homologous or heterologous to the host in question. If homologous to the host cell, i.e. produced by the host cell in nature, it will typically be operably connected to another promoter sequence or, if applicable, another secretory signal sequence and/or terminator sequence than in its natural environment. The term "homologous" is intended to include a DNA sequence encoding an enzyme native to the host organism in question. The term "heterologous" is intended to include a DNA sequence not expressed by the host cell in nature. Thus, the DNA sequence may be from another organism, or it may be a synthetic sequence.

The host cell into which the DNA construct or the recombinant vector of the invention is introduced may be any cell which is capable of producing the present enzyme and includes bacteria, yeast, fungi and higher eukaryotic cells.

Examples of bacterial host cells which, on cultivation, are capable of producing the enzyme of the invention are gram-positive bacteria such as strains of Bacillus, such as strains of *B. subtilis, B. licheniformis, B. lentus, B. brevis, B. stearothermophilus, B. alkalophilus, B. amyloliquefaciens, B. coagulans, B. circulans, B. lautus, B. megatherium* or *B. thuringiensis,* or strains of Streptomyces, such as *S. lividans* or *S. murinus,* or gram-negative bacteria such as *Echerichia coli.* The transformation of the bacteria may be effected by protoplast transformation, electroporation, conjugation, or by using competent cells in a manner known per se (cf. Sambrook et al., supra).

When expressing the enzyme in bacteria such as *E. coli,* the enzyme may be retained in the cytoplasm, typically as insoluble granules (known as inclusion bodies), or may be directed to the periplasmic space by a bacterial secretion sequence. In the former case, the cells are lysed and the granules are recovered and denatured after which the enzyme is refolded by diluting the denaturing agent. In the latter case, the enzyme may be recovered from the periplasmic space by disrupting the cells, e.g. by sonication or osmotic shock, to release the contents of the periplasmic space and recovering the enzyme.

When expressing the enzyme in gram-positive bacteria such as Bacillus or Streptomyces strains, the enzyme may be retained in the cytoplasm, or may be directed to the extracellular medium by a bacterial secretion sequence. In the latter case, the enzyme may be recovered from the medium as described below.

Suitable eukaryotic cells are in particular fungal cells such as yeasts. Examples of suitable yeast cells include cells of Saccharomyces spp., in particular strains of *Saccharomyces cerevisiae, Saccharomyces kluyveri, Sacchromyces uvarum,* or Schizosaccharomyces spp., such as *Schizosaccharomyces pombe.*

Methods for transforming yeast cells with heterologous DNA and producing heterologous polypeptides there from are described, e.g. in U.S. Pat. No. 4,599,311, U.S. Pat. No. 4,931,373, U.S. Pat. No. 4,870,008, U.S. Pat. No. 5,037,743, and U.S. Pat. No. 4,845,075, all of which are hereby incorporated by reference. Transformed cells are selected by a phenotype determined by a selectable marker, commonly drug resistance or the ability to grow in the absence of a particular nutrient, e.g. leucine. A preferred vector for use in yeast is the POT1 vector disclosed in U.S. Pat. No. 4,931,373. The DNA sequence encoding the polypeptide of the invention may be preceded by a signal sequence and optionally a leader sequence, e.g. as described above.

Further examples of suitable yeast cells are strains of Candida spp., such as *Candida utilis, Candida boidinii,* or strains of Kluyveromyces spp., such as *K. lactis,* or strains of Hansenula spp., e.g. *H. polymorpha,* or strains of Pichia spp., e.g. *Pichia methanolica, Pichia angusta, Pichia pastoris* or *Pichia anomala,* Yarrowia spp., such as *Yarrowia lipolytica* (cf. Gleeson et al., J. Gen. Microbiol. 132, 1986, pp. 3459–3465; U.S. Pat. No. 4,882,279).

Method of Producing Isoamylase

The present invention provides a method of producing an isolated enzyme according to the invention, wherein a suitable host cell, which has been transformed with a DNA sequence encoding the enzyme, is cultured under conditions permitting the production of the enzyme, and the resulting enzyme is recovered from the culture.

When an expression vector comprising a DNA sequence encoding the enzyme is transformed into a heterologous host cell it is possible to enable heterologous recombinant production of the enzyme of the invention.

Thereby it is possible to make a highly purified isoamylase composition, characterized in being free from homologous impurities.

According to the present invention the heterologous host cell may e.g. be a strain of *E. coli,* Bacillus spp., Saccharomyces, Candida, Pichia, Hansenula.

The medium used to culture the transformed host cells may be any conventional medium suitable for growing the host cells in question. The expressed isoamylase may conveniently be secreted into the culture medium and may be recovered therefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

Isolated Pure Culture

The invention also relates to an isolated substantially pure biological culture of the *Escherichia coli* strain DSM 11971 harboring an isoamylase encoding DNA sequence (the isoamylase encoding part of the DNA sequence cloned into plasmid pUC19 present in *Escherichia coli* DSM 11971) obtained from a strain of the bacteria Rhodothermus (it will be understood that any mutant of said *E. coli* strain having retained the isoamylase encoding capability is considered to be included in the present invention); and to an isolated substantially pure biological culture of *Rhodothermus marinus* DSM 4252 (it will be understood that any mutant of said *Rhodothermus marinus* strain having retained the isoamylase encoding capability is considered to be included in the present invention),from which the DNA sequence presented as SEQ ID NO: 3 has been obtained.

Cloning of a DNA Sequence from a Strain of Sulfolobus

The invention also relates to a cloned DNA sequence encoding an enzyme with isoamylase activity derived from a strain of Sulfolobus. The DNA sequence may be derived from a strain of *Sulfolobus acidocaldarius* or *Sulfolobus solfataricus.*

The sequences may be the DNA sequences encoding an isoamylase from *Sulfolobus acidocaldarius* disclosed in Biochim. Biophys. Acta, 1291, p.177–181 (1996), it may be the DNA sequence from *Sulfolobus solfataricus* available in GeneBank under the Accession no. Y08256.

The invention further relates to a recombinant expression vector comprising a cloned DNA sequence derived from Solfolobus as described above, in particular the DNA sequence disclosed in Biochim. Biophys. Acta, 1291, p.177–181 (1996) and GeneBank, Accession no. Y08256.

Furthermore the invention relates to a host cell comprising a cloned DNA sequence from Sofolobus of the invention or a recombinant expression vector comprising a DNA sequence from Sofolobus of the invention.

The host of the invention may be a eukaryotic cell, in particular a fungal cell, such as a yeast cell or a filamentous fungal cell. Specifically the host cell may be selected within the group including a strain of Saccharomyces, Candida, Pichia, Hansenula, Fusarium, Aspergillus, Trichoderma, in particular a strain of *Saccharomyces cerevisiae, Candida utilis, Candida boidinii, Pichia methanolica, Pichia an-gusta, Pichia pastoris, Pichia anomala,* Fusarium ATTC 20334, *Aspergillus niger, Asper-gillus oryzae, Trichoderma harzianum* or *Trichoderma reesei.*

Finally the invention relates to method of producing an enzyme exhibiting isoamylase activity encoded by a cloned DNA sequence of the invention, the method comprising culturing a host cell of the invention, under conditions permitting the production of the enzyme, and recovering the enzyme from the culture.

Cloning of the *Sulfolobus acidocaldarius* DNA sequence disclosed in Biochim. Biophys. Acta, 1291, p.177–181 (1996) is described below.

MATERIALS AND METHODS

Enzymes

Promozyme®: Pullulanase (available from Novo Nordisk) derived from *Bacillus acidopullulyticus* (described in EP 63,909).

AMG: *Aspergillus niger* glucoamylase (available from Novo Nordisk A/S)

α-amylase: *Bacillus licheniformis* α-amylase having the following mutations:

A1*+N2*+L3V+M15T+R23K+S29A+A30E+Y31H+A33S+E34D+ H35I+H156Y+A181T+N190F+A209V+Q264S (see WO 97/41213 from Novo Nordisk A/S).

Deposited Micro-organism(s)

Transformant Strain

An *E. coli* DH12S comprising the full length isoamylase cloned from *Rhodothermus marinus* DSM 4252 has been deposited according to the Budapest Treaty at the Deutshe Sammlung von Mikroorganismen und Zellkulturen GmbH., Mascheroder Weg 1b, D-38124 Braunschweig Federal Republic of Germany, (DSM).

Deposit date: 29.01.98

Depositor's ref.: NN049374

DSM designation: *Escherichia coli* DSM 11971

*E. coli* Top 10 (Invitrogen)

Plasmid pBAD/Myc-His A,B,C (Invitrogen)

pUC19 (Invitrogen)

Solutions and Media

LB medium: 1% bacto tryptone, 0.5% bacto yeast extract, 1% NaCl, pH 7.

SOB medium: 2% bacto tryptone, 0.5% yeast extract, 0.05% NaCl, 2.5 mM KCl, 10 mM MgSO4, pH 7.

Iodine solution: 2 ml of distilled water, 40 ml of 0.2% $I_2$, 2.0% KI and 0.2% $H_2SO_4$.

Methods

General Molecular Biology Methods

Unless otherwise mentioned the DNA manipulations and transformations were performed using standard methods of molecular biology (Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for Bacillus". John Wiley and Sons, 1990).

Enzymes for DNA manipulations were used according to the specifications of the suppliers.

Enzymes for DNA Manipulations

Unless otherwise mentioned all enzymes for DNA manipulations, such as e.g. restriction endonucleases, ligases etc., are obtained from New England Biolabs, Inc.

EXAMPLES

Example 1

PCR screening for Isoamylase a) PCR Conditions

To provide thermostable isoamylases an alignment of five known isoamylases of which the protein sequence data is available was made (see Table 1).

TABLE 1

| 1 *Pseudomonas amyloderamosa* | Biochim. Biophys. Acta, 1087, p. 309–315 (1990) |
|---|---|
| 2 *Pseudomonas* sp. | European patent publication number: EP 0 302 838 A2 |
| 3 *Flavobacterium* sp. | International patent publication number: WO 96/03513 |
| 4 *Flavobacterium odoratum* | Japanese patent publication number: JP08023981-A |
| 5 *Sulfolobus acidocaldarius* | Biochim. Biophys. Acta, 1291, p. 177–181 (1996) |

Two conserved regions (see i6 and i7 below) without too much degeneration were identified.

i6: RFNPNKL(V)L (residues 136–143 of *Pseudomonas amyloderamosa* isoamylase) SEQ ID NO:15 i7: NYWGYMT (residues 272–278 of *Pseudomonas amyloderamosa* isoamylase) SEQ ID NO:16

PCR primers were designed based on said conserved regions.

primer iso 6:
  5'-gitt(tc)aa(tc)cciaa(tc)aa(ag)(tcg)ti(tc)t-3' (SEQ ID NO: 1)

primer iso 7:
  5'-gtcat(ga)taicccca(ag)ta(ga)tt -3' (SEQ ID NO:2)

Genomic DNA stocks of a number of bacterial strains were prepared with the method described in "Current Protocols in Molecular Biology, unit 2.4 Preparation of Genomic DNA from Bacteria". PCR conditions are shown follows,

| Genomic DNA | 200 ng |
| primer iso 6 | 2 µl of 100 pmole/µl (200 pmole) |
| primer iso 7 | 2 µl of 100 pmole/µl (200 pmole) |
| 2.5 mM dNTP mixture | 2 µl |
| 10 x Gene-Taq buffer | 10 µl |
| Gene-Taq DNA polymerase | 2 units |

$H_2O$ was added to a total of 100 µl

PCR cycles were run at the following program:

94° C. for 5 min, 50° C. for 1.5 min, 72° C. for 3 minutes, and 94° C. for 1.5 min, 50° C. for 1.5 min, 72° C. for 3 min repeat 24 times, and then 94° C. for 1.5 min, 50° C. for 1.5 min, 72° C. for 15 min.

Ten ml aliquots of each PCR are applied on an 1.5% agarose gel to visualise the expected 450 bp fragment.

b) Sequencing of Positives

The purified fragments were ligated to T-vector (Novagen) with DNA ligation kit (Takara Ver2.).

Using the ligated mixture, the transformation of competent E. coli JM109 were carried out by Hanahan's method. The transformants bearing the fragments were cultivated and the plasmids were prepared with QIAgen miniprep kit. The purified plasmids are utilized as the template DNA in cycle sequencing reaction (PRISM Dyedeoxy Terminator Cycle Sequencing Mix) of both strands using Universal primers. The sequence was determined with ABI PRISM 310 Genetic Analyzer (Perkin Elmer) and they were aligned with the software MEgAlign (DNA Star, Laser gene).

Five strains yielded fragments of the expected size of about 450 bp, and these were purified, sequenced, and aligned. The fragments had homology with published isoamylase sequences as Table 2. The calculation of homology was done as described previously in this specification.

TABLE 2

| Strains identified | | % homology with* | | | | |
| --- | --- | --- | --- | --- | --- | --- |
| | | 1 | 2 | 3 | 4 | 5 |
| Flavobacterium sp. | IFO 14590 | 37.2 | 37.2 | 35.8 | 34.3 | 45.0 |
| Flavobacterium devorans | ATCC 10829 | 38.7 | 38.7 | 37.2 | 38.0 | 44.8 |
| Xanthomonas campestris | ATCC 31922 | 37.2 | 37.2 | 40.9 | 37.2 | 49.7 |
| Rhodothermus marinus | DSM 4252 | 38.0 | 38.0 | 36.5 | 35.0 | 52.4 |
| Rhodothermus obamensis | JCM 9785 | 38.0 | 38.0 | 36.5 | 35.0 | 52.4 |

*numbers refer to Table 1

The a.a. sequences of the enzymes shown in Table 2 is shown in the Sequence Listing below:

Flavobacterium sp. IFO 14590: SEQ ID NO: 11
Flavobacterium devorans ATCC 10829: SEQ ID NO: 12
Xanthomonas campestris ATCC 31922: SEQ ID NO: 13
Rhodothermus marinus DSM 4252: SEQ ID NO: 4
Rhodothermus obamensis JCM 9785: SEQ ID NO: 14

Among the five, Rhodothermus marinus DSM 4252 (SEQ ID NO: 4) and Rhodothermus obamensis JCM 9785 (SEQ ID NO: 14) with the highest optimum growth temperature (65–70° C.) were selected. As the two fragment sequences are almost identical, only one of them, Rhodothermus marinus DSM 4252, was further employed for cloning and expression.

Example 2
Cloning of a Gene Encoding a Thermostable Isoamylase and its Expression in E. coli Using the PCR screening method for isoamylase described above it was found that Rhodothermus marinus, having a growth temperature above 60° C., has a gene encoding an isoamylase. The isoamylase gene from Rhodothermus marinus DSM 4252 was cloned with colony hybridisation technique as follows:

a) Southern Hybridisation

Rhodothermus marinus genomic DNA was prepared according to the methods described in "Current Protocols in Molecular Biology, unit 2.4 Preparation of Genomic DNA from Bacteria". Southern blotting was carried out with the methods described in "Current protocols in Molecular Biology, unit 2.9.1 Southern blotting". The membrane with genomic DNA fragments was prehybridised in a hybridisation solution (5× SSC, 0.5% blocking reagent (Boehringer Mannheim), 0.1% N-lauroylsarcosine, and 0.02% SDS) at 68° C. for 1 hour. Then it was hybridised in the hybridisation solution including 10 ng/ml of the probe which was the fragment obtained by PCR screening labeled by DIG DNA labeling Mix (Boehringer Mannheim) at 68° C. for 12 hours. Then the probe was detected by DIG Nucleic Acid Detection Kit (Boehringer Mannheim).

Southern hybridisation showed that about 7 kbp EcoRI digested fragment of genomic DNA hybridized with the probe. The EcoRI digested genomic DNA (6 to 8 kbp) were extracted from 1% agarose gel with Gel extraction kit (QIAgne).

b) Colony Hybridisation

The fragments digested by EcoRI was ligated into pUC 19 to make a genomic DNA library. It was transformed to E. coli DH12S Electromax (GIBCO BRL) by electroporation and plated onto LB plate including 200 mg/ml ampicillin. After overnight cultivation at 37° C. these colonies were replicated to a nylon membrane. It was soaked into denaturing solution (1.5 M NaCl and 0.5 M NaOH) for 7 min and then neutralising solution (1.5 M NaCl, 0.5M Tris-HCl pH 7.2), and 0.001M EDTA). Hybridisation conditions were same as southern hybridisation.

Among 1000 transformants that were screened by colony hybridisation, 3 colonies hybridised with the probe.

c) Analysis by Restriction of Positive Clones

Plasmids were prepared from 3 transformants, and southern hybridization showed that these 3 transformants had the same insertion of a 7 kbp EcoRI fragment which hybridised with the probe.

The restriction enzyme map of one of the positive clones named pRI5A, was determined and it is shown in FIG. 1.

d) Sequencing of Isoamylase Gene

The isoamylase gene nucleotide sequence was determined using ABI PRISMTM 310 Genetic Analyzer. The sequencing reaction was carried out using dye terminator cycle sequencing FS ready reaction kit (P/N 402153). The reaction was followed by the protocol mentioned by PE Applied Biosystems.

Primers were designed from the determined sequence of the probe location. Determined 2178 bp of ORF and the deduced amino acid sequence are shown in SEQ ID NO: 3. The sequence of the probe for hybridisation is nt.342–770 of SEQ ID NO:3.

e) Expression Vector pBAD/Myc-His B was used for expression.

f) Cloning of Isoamylase Gene for Expression

The R. marinus isoamylase gene was cloned by PCR from pRI5A. The primers

Primer N: gtcagtagcccatggcacattagcgc (SEQ ID NO: 5)
Primer BX2: ctcggccggactagatctgtcttc (SEQ ID NO: 6)

NcoI site was designed in the primer N. ATG of the NcoI site was used as the start codon. Due to the NcoI site (ccatgg), the second amino acid Serine changed to Alanine. In the primer BX2, the XbaI site was designed behind the stop codon.

PCR was carried out the following conditions using primer N and primer BX2.

| | |
|---|---|
| Genomic DNA | 100 ng |
| sense primer | 1 ml of 100 pmole/ml (100 pmole) |
| antisense primer | 1 ml of 100 pmole/ml (100 pmole) |
| 2.5 mM dNTP mixture | 2 ml |
| 10x buffer | 5 ml |
| Taq DNA polymerase | 1 unit |

H2O was added to total up to 50 ml

PCR cycles were run at the following program.

94° C. 5 min, 60° C. 1.5 min, 72° C. 3 min, then 94° C. 1.5 min, 60° C. 1.5 min, 72° C. 3 min, repeat 24 times, and 94° C. 1.5 min, 60° C. 1.5 min, 72° C. 15 min.

The obtained fragment (about 2kbp) was treated with NcoI and XbaI, then it was ligated with pBAD/Myc-His B and transformant harbouring the plasmid named pBX2 was obtained. The host for expression was *E. coli* Top10.

g) Expression Condition

The transformant with pBX2 was cultivated in 100 ml of LB medium, including 200 mg/ml ampicillin at 37° C. for overnight. One ml seed culture was inoculated to 100 ml of SOB medium including 200 mg/ml ampicillin and was cultivated at 37° C. for 2.5 hours. Then 100 ml of 20% arabinose was added to induce the recombinant proteins. The cultivation was continued at 37° C. overnight. Next day, the cells were harvested by centrifugation. The cells were washed with 50 mM Sodium citrate buffer (pH 5.0). Then the cells were suspended with the same buffer including 1 mg/ml of lysozyme and stored at 4° C. for 1 hour. After lysozyme treatment the cells were disrupted by ultrasonication. The supernatant was obtained by centrifugation at 18,000 rpm for 30 minutes. The debris was disrupted by ultrasonication again. The ultrasonication treatment was repeated once more. Finally, the supernatant was gathered and it was heated at 70° C. for 1 hour to remove the proteins from the host strain. Centrifugation at 18,000 rpm for 30 minutes was carried out and the supernatant constituted the crude isoamylase sample.

Example 3

Characterisation of the Cloned *Rhodothermus marinus* Isoamylase a) Assay Method Isoamylase character was investigated by the following assay method. 250 ml of 1% amylopectin from waxy rice and 50 ml of 50 mM citrate buffer were pre-incubated for 5 minutes. The reaction was started by adding 50 ml of enzyme solution. After 10 minutes of incubation, 40 ml of reaction mixture was put into the Iodine solution (2 ml of D.W. and 40 μl of 0.2% $I_2$, 2.0% KI and 0.2% $H_2SO_4$). Then its OD600 value was measured. Distilled water was added instead of enzyme solution in the blank.

b) pH Optimum at 50° C.

Figure 2:
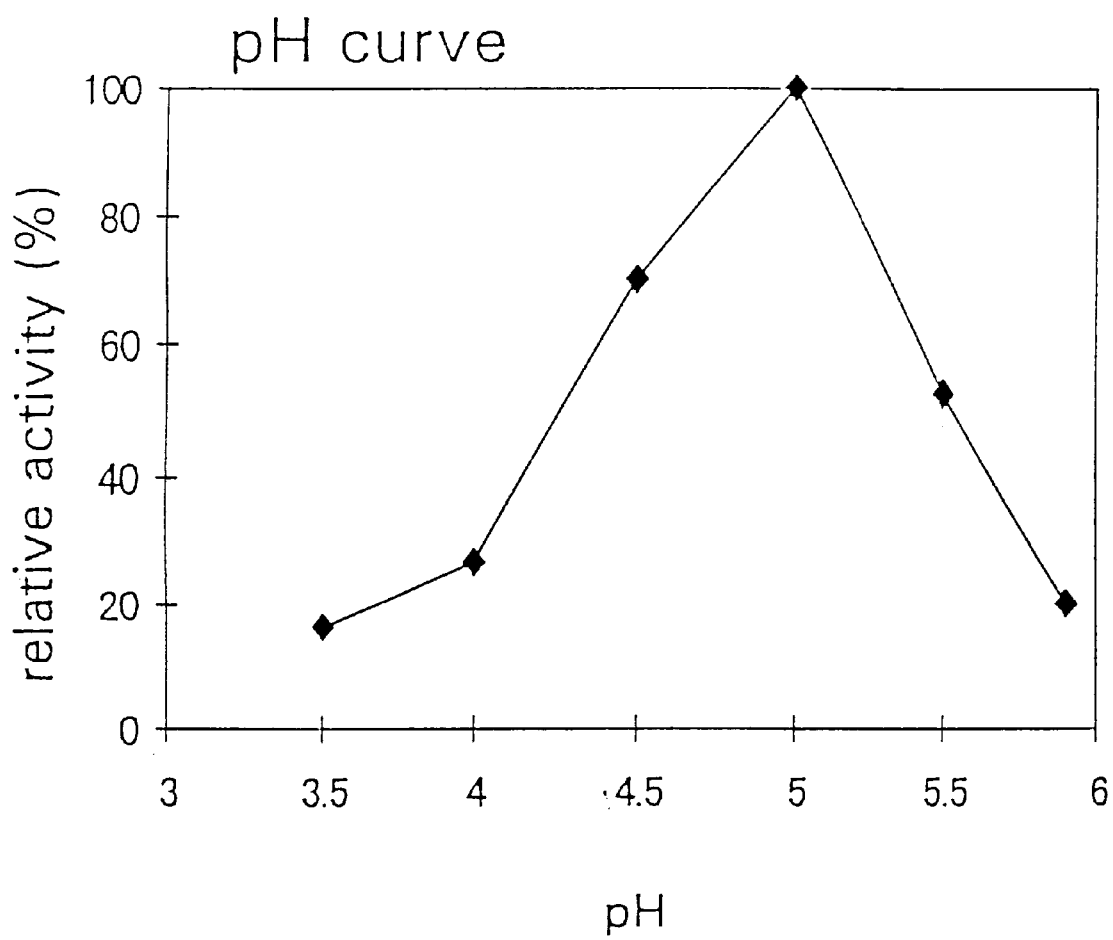
FIG. 2 shows the pH curve of *R. marinus* isoamylase.

The pH optimum of the Rhodothermus isoamylase was determined. The reaction was carried out at 50° C. The pH optimum was determined to pH 5.0. The pH curve is shown in FIG. 2.

c) Temperature Optimum at pH 5.0

Figure 3:
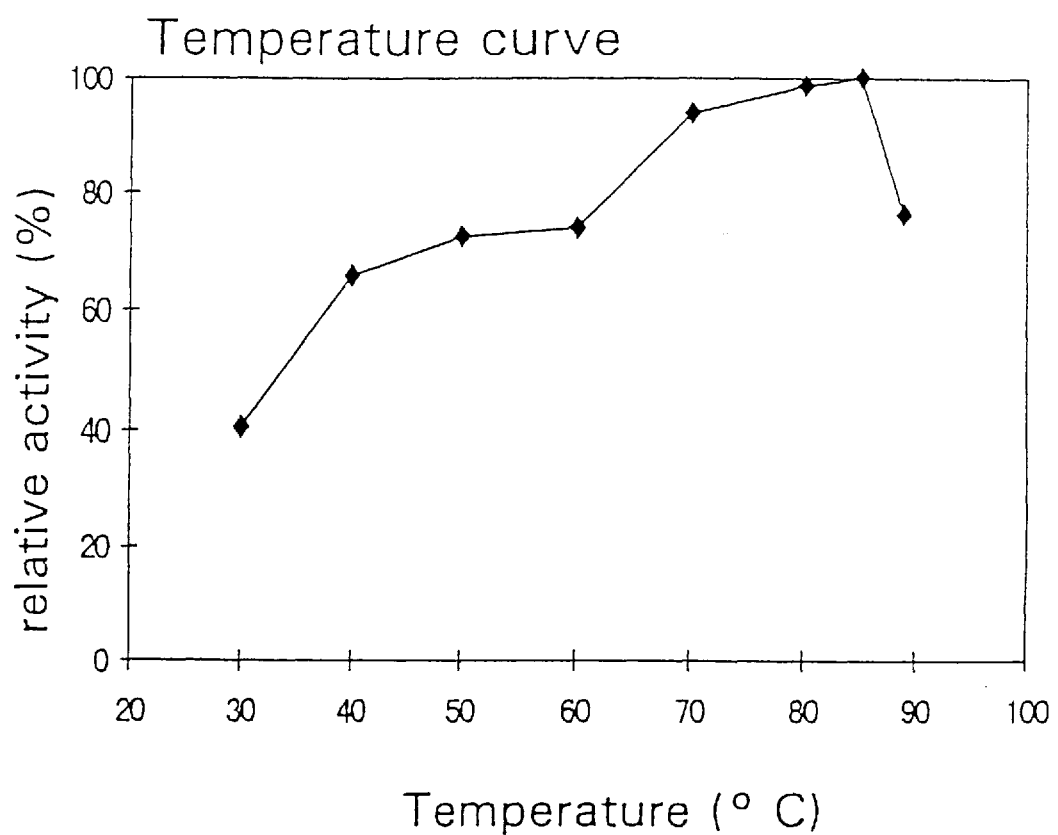
FIG. 3 shows the temperature curve of *R. marinus* isoamylase.

Temperature optimum of the Rhodothermus isoamylase was determined. The reaction was carried out at pH 5 at between 30°–89° C. The optimum temperature was determined to be around 85° C. The temperature curve is shown in FIG. 3.

d) Molecular Weight and pI

The $M_w$ of Rhodothermus was determined by SDS PAGE. SDS PAGE was carried out using Phast system with gradient gel 10–15 (Pharmacia Biotech). The $M_w$ of the recombinant protein was calculated to 80 kDa.

e) N-terminal Amino Acid Sequence of the Recombinant Protein

N-terminal amino acid sequence of the recombinant protein was determined. The result was identical with the deduced amino acid sequence from nucleotide sequence (Serine was changed to Alanine because of primer N).

Example 4

Starch Conversion Using the Rhodothermus Isoamylase

To test the effect of the *Rhodothermus marinus* isoamylase on the glucose yield in starch conversion processes a standard two step starch conversion process was performed with/without adding isoamylase in the liquefaction and saccharification steps.

The Standard Starch Convention Process

A 30% w/w DE 10 maltodextrin prepared from common corn starch was used as the starting material.

The liquefaction step was carried out at 80° C., pH 5.5, for 90 minutes in the presence of an α-amylase variant (8 microgram/gram Dry Solid).

The saccharification step was carried out at 60° C., pH 4.5, for a period of 48 hours in the presence of AMG (0.18 AGU/gram Dry Solid) with/without addition of a pullulanase (Promozyme®) (0.06 PUN/gram Dry Solid).

In Table 3 shown in FIG. 7 the tests performed and effect of the isoamylase on the DP1, DP2, DP3 and DP4+ yields are listed.

Addition of Isoamylase in the Liquefaction Step

As can be seen from said Table 50 or 200 micrograms/gram Dry Solid *Rhodothermus marinus* isoamylase was added in TEST 3, 4, 8 and 9 during liquefaction. In TEST 1, 5 and 7 the α-amylase was inactivated after 90 minutes of liquefaction by adjusting the pH to 3.0 for 15 minutes at 80° C.

In all tests where isoamylase is added a lower DP4+ yield is obtained. This indicate that the substrate has been more accessible to the α-amylase and the AMG.

By comparing TEST 2 (i.e. no isoamylase added) with 3 and 4 (i.e. isoamylase added) it can be seen that the DP3 (i.e. panose) yield is reduced from 1.2% to 1.0% and 0.9%, respectively, and that the DP1 (i.e. glucose) yield is increased from 96.3% to 96.5% and 96.8%, respectively.

Addition of Isoamylase in the Saccharification Step

In TEST 7 isoamylase was added during the saccharification step. By comparing TEST 7 with TEST 5, it can be seen that the DP3 (i.e. panose) yield is reduced from 0.5% to 0.4%, and that the DP1 (i.e. glucose) yield is increased from 93.2% to 94.8%

Conclusion

The addition of the *Rhodothermus marinus* isoamylase during starch conversion results in an increased glucose yield.

Example 5

Cloning and Expression of *Sulfolobus acidocaldarius* Isoamylase Gene a) Cloning of Isoamylase Gene The isoamylase gene from *Sulfolobus acidocaldarius* was cloned by PCR. The primers were designed based on the sequence shown in the article of Table 1.

primer SINH:

5'-gtatatcaaagcttatgaaagatcgaccattaaagcctg-3' (SEQ ID NO:7) primer SICX:

5'-ggttgtctagatcactggaactctatcctcctgta-3' (SEQ ID NO:8)

PCR was carried out by the procedure described in Example 2-f.

The right size fragment (about 2 kb) was obtained and it was purified using PCR purification kit (QIAgen). The purified fragment was treated with HindIII and XbaI.

b) Construction of Expression Vector

Expression vector was constructed from pJSO26 which has TPI promotor (Annals New York Academy of Sciences, vol782, p202 J. S. Okkels). pJSOHX was made from pJSO26 to delete BamHI site and add HindIII site using following 2 oligonucleotide as casset, gatcaagcttggaat-tcgctcgagct (SEQ ID NO: 9) and ctagagctcgagcgaattccaagctt (SEQ ID NO: 10).

Figure 4:
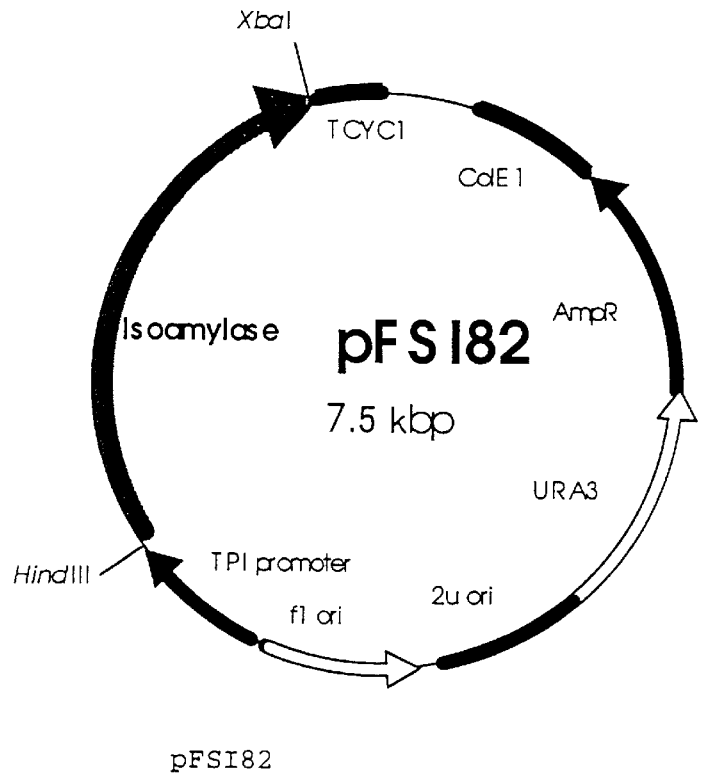
FIG. 4 shows the expression vector, pFSI82.

Cloned gene from *Sulfolobus acidocaldarius* was inserted at Hind III and XbaI site of pJSOHX and expression vector named pFSI82 was obtained. PFSI 82 was transformed to *Saccharomyces cerevisiae* YNG318. pFSI82 map is shown in FIG. 4.

b) Expression Procedure

The transformant harbouring pFSI82 was cultivated in 100 ml YPD for 2 days. The cells were harvested by centrifugation at 5,000 rpm for 5 min and spheroplast was made with a basic protocol (Bio manual series 10, Yodosha).

The spheloplast was disrupted by ultrasonication and cell extract was heat treated at 70° C. for 30 min. The debris was removed by centrifugation at 14,000 rpm for 30 min and the supernatant constituted the crude isoamylase sample.

Example 6

Characterization of the Cloned *Sulfolobus acidocaldarius* Isoamylase

The recombinant isoamylase was characterized using the assay described in Example 3-a.

a) pH Optimum at 70° C.

Figure 5:
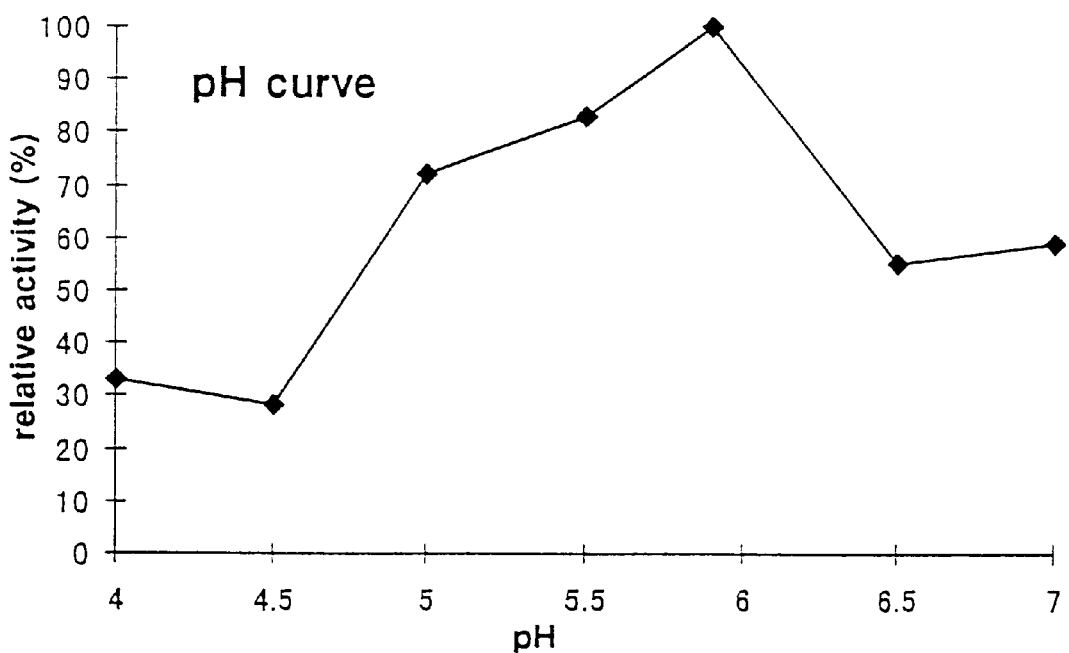
FIG. 5 shows the pH curve of *Sulfolobus acidocaldarius* isoamylase.

The pH optimum of the *Sulfolobus acidocaldarius* isoamylase was determined. The Reaction was carried out at 70° C. The checked pH was between pH 3.5–7.5. The pH optimum was determined to pH 5.5. The pH curve is shown in FIG. 5.

b) Temperature Optimum at pH 5.5

Figure 6:
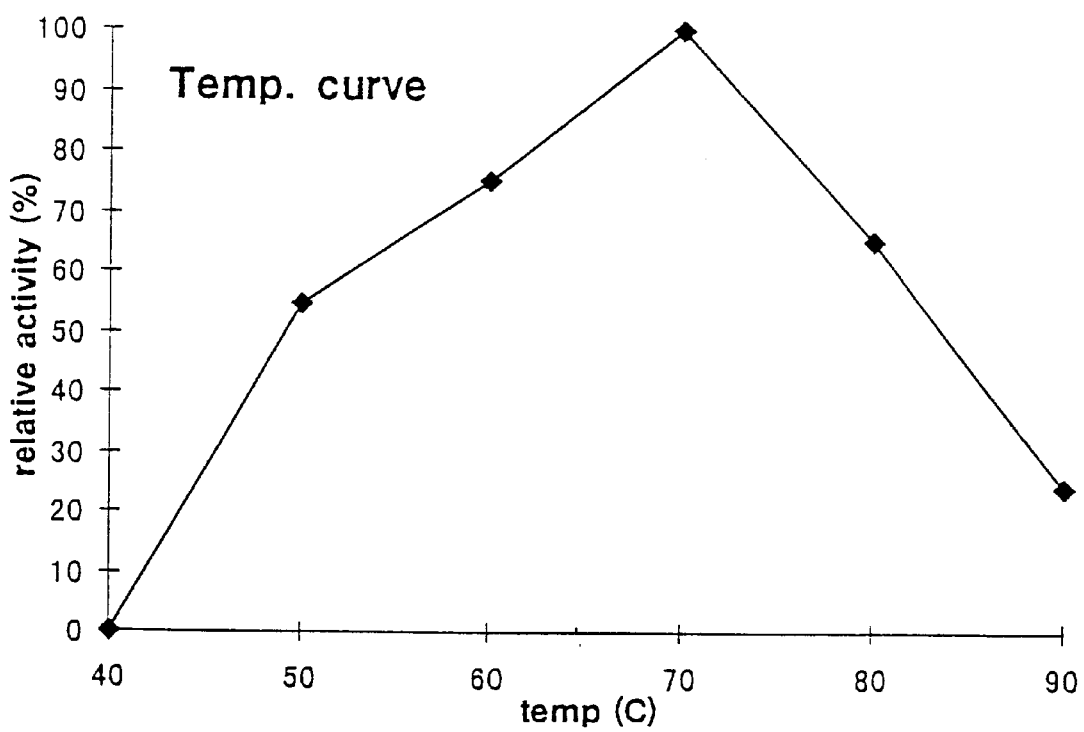
FIG. 6 shows the temperature curve of *S. acidocaldarus* isoamylase.

Temperature optimum of the Sulfolobus isoamylase was determined. The reaction was carried out at pH5.5 at between 40°–90° C. The optimum temperature was determined to be around 70° C. The temperature curve is shown in FIG. 6.

What is claimed is:

1. An isolated nucleic acid which comprises a sequence selected from the group consisting of:
   (a) a sequence which is present in plasmid pUC19 in *Escherichia coli* DSM 11971 and which encodes an isoamylase or a fragment thereof having isoamylase activity;
   (b) a sequence of nucleotides 1–2178 of SEQ ID NO:3 or its complementary strand;
   (c) a sequence encoding a polypeptide having an amino acid sequence of SEQ ID NO:4 or a fragment thereof having isoamylase activity;
   (d) a sequence which encodes an isoamylase and which is at least 80% homologous with sequences (a) or (b), wherein the homology is determined using GAP with a GAP creation penalty of 5.0 and a GAP extension penalty of 0.3; and
   (e) a sequence which encodes a polypeptide having isoamylase activity and hybridizes under medium stringency conditions with nucleotides 1–2178 of SEQ ID NO:3.

2. A nucleic acid of claim 1, wherein the sequence is present in plasmid pUC19 in *Escherichia coli* DSM 11971 and encodes an isoamylase or a fragment thereof having isoamylase activity.

3. A nucleic acid of claim 1, wherein the sequence is nucleotides 1–2178 of SEQ ID NO:3 or its complementary strand.

4. A nucleic acid of claim 1, wherein the sequence encodes a polypeptide having an amino acid sequence of SEQ ID NO:4 or a fragment thereof having isoamylase activity.

5. A nucleic acid of claim 1, wherein the sequence encodes an isoamylase and is at least 80% homologous with nucleotides 1–2178 of SEQ ID NO:3.

6. A nucleic acid of claim 5, wherein the sequence is at least 90% homologous with nucleotides 1–2178 of SEQ ID NO:3.

7. A nucleic acid of claim 6, wherein the sequence is at least 95% homologous with nucleotides 1–2178 of SEQ ID NO:3.

8. A nucleic acid of claim 7, wherein the sequence is at least 97% homologous with nucleotides 1–2178 of SEQ ID NO:3.

9. A nucleic acid of claim 5, which is obtained from a microorganism selected from the group consisting of a fungus, a yeast, a bacterium, and an archaebacterium.

10. A nucleic acid of claim 9, which is obtained from a strain of the order Cytophagales.

11. A nucleic acid of claim 10, wherein the strain is a *Rhodothermus marinus* or *Rhodothennus obamensis* strain.

12. A nucleic acid of claim 11, wherein the sequence encodes a polypeptide having isoamylase activity and hybridizes under medium stringency conditions with nucleotides 1–2178 of SEQ ID NO:3.

13. A nucleic acid of claim 12, wherein the sequence hybridizes under high stringency conditions with nucleotides 1–2178 of SEQ ID NO:3.

14. A nucleic acid of claim 13, which is obtained from a strain of the order Cytophagales.

15. A nucleic acid of claim 14, wherein the strain is a *Rhodothermus marinus* or *Rhodothermus obamensis* strain.

16. A recombinant vector comprising a nucleic acid sequence of claim 1.

17. A host cell comprising a vector of claim 16.

18. A host cell of claim 17, wherein the cell is a yeast cell or a filamentous fungal cell.

19. A host cell of claim 18, wherein the cell is selected from the group consisting of Fusarium, Aspergillus, Trichoderma, Saccharomyces, Candida, Pichia, and Hansenula cells.

20. A host cell of claim 19, wherein the cell is selected from the group consisting of Fusarium sp. having the identifying characteristic of Fusarium ATCC 20334, *Aspergillus niger, Aspergillus oryzae, Trichoderma harzianum, Trichoderma reesei, Saccharomyces cerevisiae, Candida utilis, Candida boidinii, Pichia methanolica, Pichia angusta, Pichia pastoris* and *Pichia anomala*.

21. A host cell of claim 17, wherein the cell is a prokaryote selected from the group consisting of Bacillus, Lactobacillus, Brevibacillus, Streptomyces, and Escherichia.

22. A host cell of claim 21, wherein the cell is selected from the group consisting of *Bacillus subtilis, Bacillus stearothernophilus, Bacillus licheniformis, Bacillus lentus,* and *Escherichia coli*.

23. A method for producing a polypeptide having isoamylase activity, comprising (i) culturing a cell of claim 17 under conditions permitting the production of the polypeptide, and (ii) recovering the polypeptide from the culture.

* * * * *